(12) United States Patent
Towner

(10) Patent No.: US 11,660,280 B2
(45) Date of Patent: May 30, 2023

(54) TREATMENT OF DRUG RESISTANT GLIOMAS

(71) Applicant: OKLAHOMA MEDICAL RESEARCH FOUNDATION, Oklahoma City, OK (US)

(72) Inventor: Rheal A. Towner, Piedmont, OK (US)

(73) Assignee: OKLAHOMA MEDICAL RESEARCH FOUNDATION, Oklahoma City, OK (US)

(*) Notice: Subject to any disclaimer, the term of this patent is extended or adjusted under 35 U.S.C. 154(b) by 352 days.

(21) Appl. No.: 16/647,895

(22) PCT Filed: Sep. 10, 2018

(86) PCT No.: PCT/US2018/050162
§ 371 (c)(1),
(2) Date: Mar. 17, 2020

(87) PCT Pub. No.: WO2019/060152
PCT Pub. Date: Mar. 28, 2019

(65) Prior Publication Data
US 2020/0215015 A1    Jul. 9, 2020

Related U.S. Application Data

(60) Provisional application No. 62/561,002, filed on Sep. 20, 2017.

(51) Int. Cl.
| A61K 31/205 | (2006.01) |
| A61P 35/04  | (2006.01) |
| A61P 35/00  | (2006.01) |
| A61K 47/68  | (2017.01) |
| A61K 31/495 | (2006.01) |
| A61K 45/06  | (2006.01) |
| A61K 49/10  | (2006.01) |
| G01N 33/574 | (2006.01) |

(52) U.S. Cl.
CPC .......... *A61K 31/205* (2013.01); *A61K 31/495* (2013.01); *A61K 45/06* (2013.01); *A61K 47/6803* (2017.08); *A61K 49/10* (2013.01); *A61P 35/00* (2018.01); *A61P 35/04* (2018.01); *G01N 33/57407* (2013.01); *G01N 33/57488* (2013.01)

(58) Field of Classification Search
CPC .......... A61K 31/205; A61P 35/00; A61P 35/04
See application file for complete search history.

(56) References Cited

U.S. PATENT DOCUMENTS

| 5,475,032 A | 12/1995 | Carney |
| 5,488,145 A | 1/1996 | Carney |
| 5,569,902 A | 10/1996 | Wood |
| 8,633,249 B2 * | 1/2014 | Towner ................. A61K 31/15 |
| | | 514/576 |
| 9,289,404 B2 | 3/2016 | Kopke et al. |
| 9,474,748 B2 * | 10/2016 | Towner ................. A23L 33/10 |
| 9,642,823 B2 | 5/2017 | Kopke et al. |
| 9,968,569 B2 | 5/2018 | Towner et al. |
| 10,022,346 B2 | 7/2018 | Kopke et al. |
| 10,111,843 B2 | 10/2018 | Kopke et al. |
| 10,398,659 B2 | 9/2019 | Towner et al. |
| 2007/0032453 A1 | 2/2007 | Towner et al. |
| 2008/0207714 A1 | 8/2008 | Chinnaiyan et al. |
| 2010/0076009 A1 * | 3/2010 | Towner ................. A61K 31/166 |
| | | 514/640 |
| 2012/0178803 A1 | 7/2012 | Harn et al. |
| 2014/0187631 A1 | 7/2014 | Kopke et al. |
| 2014/0200234 A1 | 7/2014 | Towner et al. |
| 2016/0158173 A1 | 6/2016 | Kopke et al. |
| 2017/0027891 A1 | 2/2017 | Towner et al. |
| 2017/0202797 A1 | 7/2017 | Kopke et al. |
| 2017/0273926 A1 | 9/2017 | Levin |
| 2017/0281583 A1 | 10/2017 | Kopke et al. |
| 2018/0228744 A1 | 8/2018 | Towner et al. |
| 2018/0256756 A1 | 9/2018 | Kopke et al. |

FOREIGN PATENT DOCUMENTS

| JP | 2013-521229 | 6/2013 |
| JP | 2012-144512 | 2/2014 |
| JP | 2015-511936 | 4/2015 |
| WO | WO 2010/028058 | 3/2010 |
| WO | WO 2011/106577 | 9/2011 |
| WO | WO 2013/110058 | 7/2013 |

(Continued)

OTHER PUBLICATIONS

Zhu, D., M. Tu, B. Zeng, L. Cai, W. Zheng, Z. Su and Z. Yu, "Up-regulation of miR-497 confers resistance to temozolomide in human glioma cells by targeting mTOR/Bcl-2", Cancer Medicine, published online: Jan. 8, 2017, 6(2), pp. 452-462. (Year: 2017).*
Office Action issued in Japanese Patent Application No. 2020-516624, dated May 25, 2022.
Annie I. Drapeau et al. "*Intra-arterial Temozolomide, Osmotic Blood-brain Barrier Disruption and Radiotherapy in a Rat F98-Glioma Model*", Clinical Cancer Drugs, vol. 4, No. 2, Jan. 9, 2018 (Jan. 9, 2018).
Extended European Search Report issued in European Patent Application No. 18858743.0, dated Feb. 21, 2020.
Odrun A. Gederaas et al., "*Photochemical internalization of bleomycin and temozolomide—in vitro studies on the glioma cell line F98*", Photochemical & Photobiological Sciences, vol. 14, No. 7, 2015, pp. 1357-1366.

(Continued)

*Primary Examiner* — Joseph R Kosack
*Assistant Examiner* — Sagar Patel
(74) *Attorney, Agent, or Firm* — ParkerHighlander PLLC

(57) ABSTRACT

The present disclosure describes the use of 2,4-disulfonyl phenyl tert-butyl nitron (2,4-ds-PBN) in the treatment of temozolomide drug resistant gliomas. The 2,4-ds-PBN may be used combined with other chemo- and radiotherapies and surgery, including temozolomide, to reduce glioma occurrence, recurrence, spread, growth, metastasis, and vascularization, and to inhibit development of temozolomide resistance.

14 Claims, 17 Drawing Sheets
Specification includes a Sequence Listing.

(56) References Cited

FOREIGN PATENT DOCUMENTS

| WO | WO 2015/169953 | 11/2015 |
|----|----------------|---------|
| WO | WO 2016/205027 | 12/2016 |
| WO | WO 2017/048778 | 3/2017 |

OTHER PUBLICATIONS

Altinoz et al., "Targeting nitric oxide and NMDA receptor-associated pathways in treatment of high grade glial tumors. Hypotheses for nitro-memantine and nitrones," *Nitric Oxide: Biology and Chemistry*, 79:68-83, 2017.

Cho et al., "NEO212, temozolomide conjugated to perillyl alcohol, is a novel drug for effective treatment of a broad range of temozolomide-resistant gliomas," *Molecular Cancer Therapeutics*, 13(8):2004-2017, 2014.

Coutinho de Souza et al., "Inhibition of Pediatric Glioblastoma Tumor Growth by the Anti-Cancer Agent OKN-007 in Orthotopic Mouse Xenografts," *PLoS One*, 10(8):e0134276, 2015.

Extended European Search Report issued in European Patent Application No. 18858743.0, dated May 21, 2020.

Floyd et al., "Nitrone-based therapeutics for neurodegenerative diseases: their use alone or in combination with lanthionines," *Free Radical Biology & Medicine*, 62:145-156, 2013.

Towner et al., "OKN-007 Increases temozolomide (TMZ) Sensitivity and Suppresses TMZ-Resistant Glioblastoma (GBM) Tumor Growth," *Translational Oncology*, 12(2):320-335, 2019.

Coutinho de Souza et al., "OKN-007 decreases free radical levels in a preclinical F98 rat glioma model," *Free Radical Biol. Med.*, 87:157-168, 2015.

Coutinho de Souza et al., "OKN-007 decreases tumor necrosis and tumor cell proliferation and increases apoptosis in a preclinical F98 rat glioma model," *J. Magn. Reson. Imaging*, 42:1582-91, 2015.

Coutinho de Souza et al., "OKN-007 decreases VEGFR-2 levels in a preclinical GL261 mouse glioma model," *Am. J. Nuclear Med. Mol. Imaging*, 5(4):363-78, 2015.

Doblas et al., "Phenyl-tert-butylnitrone induces tumor regression and decreases angiogenesis in a C6 rat glioma model," *Free Radic. Biol. Med.*, 44:63-72, 2008.

PCT International Search Report and Written Opinion issued in International Application No. PCT/US2018/050162, dated Jan. 17, 2019.

PCT Invitation to Pay Additional Fees issued in International Application No. PCT/US2018/050162, dated Nov. 13, 2018.

Szopa et al., "Diagnostic and Therapeutic Biomarkers in Glioblastoma: Current Status and Future Perspectives," *Biomed. Res. Int.*, 2017:8013575, 2017.

Towner et al., "Regression of glioma tumor growth in F98 and U87 rat glioma models by the Nitrone OKN-007," *Neuro-Oncology*, 15:3 30-40, 2013.

Wang and Shuaib, "Neuroprotective effects of free radical scavengers in stroke," *Drugs Aging*, 24:537-46, 2007.

\* cited by examiner

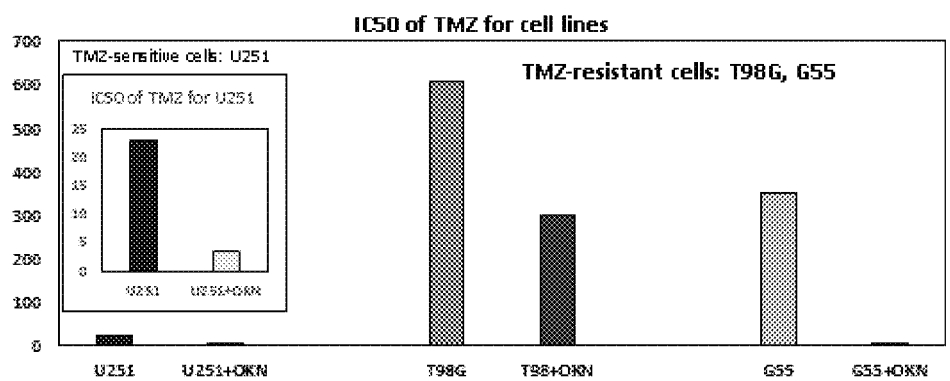
OKN-007: MW 381.33
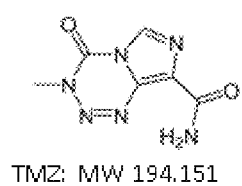
TMZ: MW 194.151
FIG. 8

FIGS. 13A-B

FIGS. 14Ai-Diii

FIGS. 15Ai-E

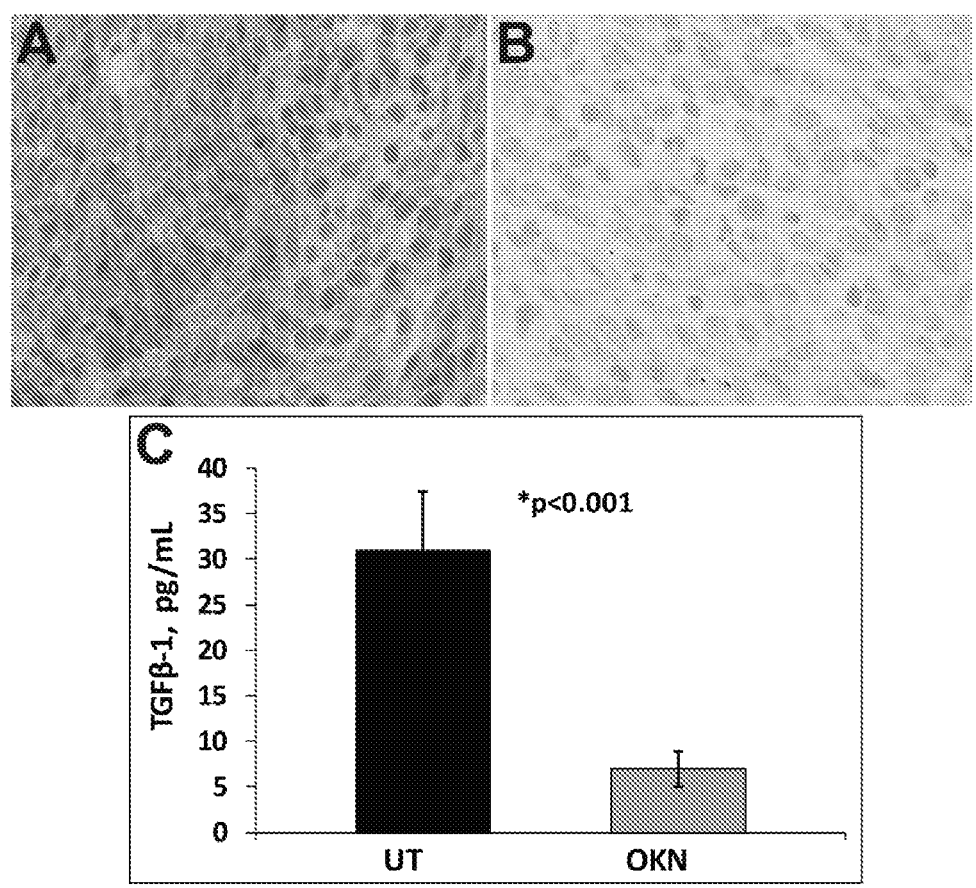
FIGS. 21A-C

SEQUENCE LISTING

<160> NUMBER OF SEQ ID NOS: 6

<210> SEQ ID NO 1
<211> LENGTH: 25
<212> TYPE: DNA

```
<213> ORGANISM: Artificial Sequence
<220> FEATURE:
<223> OTHER INFORMATION: Synthetic polynucleotide

<400> SEQUENCE: 1
gtcggacagc ctcaccaaac agagc                                          25

<210> SEQ ID NO 2
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 2
gttaacttga tccaaagctc tgag                                           24

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
gggtctgcac gaaataaagc                                                20

<210> SEQ ID NO 4
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 4
ctccggacct ccgagaac                                                  18

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
gtcctagtcc ggcgacttcc                                                20

<210> SEQ ID NO 6
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 6
cttgtctggg caggcccttt gc                                             22
```

TREATMENT OF DRUG RESISTANT GLIOMAS

This application claims benefit of priority to U.S. Provisional Application Ser. No. 62/561,002, filed Sep. 20, 2017, the entire contents of which are hereby incorporated by reference.

REFERENCE TO A SEQUENCE LISTING

This application contains a Sequence Listing XML, which has been submitted electronically and is hereby incorporated by reference in its entirety. Said Sequence Listing XML, created on Mar. 17, 2023, is named OMRF.P0133US.xml and is ~7kB in size.

BACKGROUND

1. Field

The present disclosure relates generally to the fields of oncology and chemotherapy. More particularly, it concerns the use of 2,4-disulfonyl phenyl tert-butyl nitrone (2,4-ds-PBN) to treat drug resistant gliomas.

2. Description of Related Art

Gliomas are a diverse group of brain tumors that arise from normal "glial" cells of the brain and/or their precursor cells. The most important determinant of survival for gliomas is the "grade" of the glioma. Secondary determinants of survival are age at diagnosis, performance status, and extent of surgery. Patients with low-grade gliomas have a protracted natural history with generally long survival times, while those with high grade gliomas are much more difficult to successfully treat and have shorter survival times. All gliomas have specific signs and symptoms that are primarily related to the location and size of the glioma.

The temporal lobe gliomas, for example, may cause seizures, difficulty with speech and/or loss of memory. The frontal lobe gliomas may cause seizures, behavioral changes, weakness of the arms or legs on the opposite side of the body, and/or difficulty with speech. The occipital gliomas may cause loss of vision. The parietal gliomas may cause loss of spatial orientation, diminished sensation on the opposite side of the body, and/or inability to recognize once familiar objects or persons.

Astrocytomas are glioma tumors that arise from brain cells called astrocytes or their precursors. Astrocytes are cells in the central nervous system that support neuronal function. Astrocytomas can be graded by histologic features that signify increasing malignancy into astrocytoma, anaplastic astrocytoma, or glioblastoma multiforme. Anaplastic astrocytoma and glioblastoma multiforme are considered high-grade gliomas while the astrocytoma is considered to be a low-grade glioma. High-grade tumors grow rapidly and can easily infiltrate and spread through the brain. Low-grade astrocytomas can also infiltrate the brain but are usually more localized and grow slowly over a long period of time. High-grade tumors are much more aggressive and require very intense therapy. The majority of astrocytic tumors in children are low-grade, whereas the majority in adults are high-grade. Astrocytomas can occur anywhere in the brain and spinal cord, however the majority are located in the cerebral hemispheres.

Oligodendrogliomas are also gliomas. They arise from oligodendrocytes and/or their cell precursors. Normal oligodendrocytes provide myelin, a fatty substance that covers nerve axons in the brain and spinal cord and allows nerves to conduct electrical impulses more efficiently. Oligodendrogliomas are classified as low grade oligodendroglioma (less aggressive) and anaplastic oligodendroglioma (more aggressive). More common than pure oligodendrogliomas are low grade and anaplastic tumors that are a mixture of astrocytoma and oligodendroglioma ("oligoastrocytomas").

Anaplastic oligodendrogliomas and mixed oligoastrocytomas are more sensitive to cytotoxic chemotherapy than astrocytomas. A high rate of response to the PCV (procarbazine (matulane), CCNU (lomustine), vincristine) chemotherapy has made the use of this regimen, if not the standard of care for these tumors, at least a very common treatment. Low grade oligodendrogliomas are also sensitive to chemotherapy, and PCV can be used when low grade tumors begin to grow despite prior surgery/radiation therapy.

The efficiency of phenyl-tert-butyl-nitrone (PBN) as a potential anti-glioma drug has been shown in the pretreatment of a rat C6 glioma implantation model (Doblas et al., 2008). MRI results from untreated rats showed the diffusive invasiveness of C6 gliomas, with some associated angiogenesis. PBN administration as a pretreatment was found to clearly induce a decrease in growth rate and tumor regression as well as preventing angiogenesis. However, post-treatment of PBN had a reduced effect (~50% of tumors had reduced tumor growth) for tumor regression compared with pre-treatment (>80% of the tumors had reduced growth). MRI findings rivaled those from histology and angiogenesis marker immunostaining evaluations.

In a more recent study, the inventor has shown that a structural analog of PBN, 2,4-ds-PBN, decreased tumor volumes and delayed tumor growth rate. 2,4-ds-PBN post-treatment was also significantly effective in increasing survival rate. This result was unexpected and surprising as sulfonated derivatives of PBN were not known to be able to readily cross the blood-brain-barrier (BBB). PBN, the parent nitrone, had been previously found to easily penetrate the BBB (Wang & Shuaib, 2007). 2,4-disulfonyl PBN (2,4-ds-PBN) is structurally related to the parent compound PBN, but contains two sulfonyl groups that make it much more water-soluble. As a result of the increased water solubility 2,4-disulfonyl PBN was initially thought to not easily pass through the BBB, as compared to PBN (Wang & Shuaib, 2007). The inventor has however demonstrated that 2,4-disulfonyl PBN can readily cross the BBB (Coutinho de Souza et al., 2015). Ideally, drugs that are to be used as anti-glioma therapy need to pass the endothelial junctions of the BBB to reach the majority of tumor cells (Cao et al., 2005), but it is possible that malignant gliomas have acquired the ability to actively degrade tight junctions by secreting soluble factors, eventually leading to BBB disruption within invaded brain tissue (Schneider et al., 2004). Specifically, 2,4-disulfonyl PBN has shown significant efficacy as a monotherapy for glioma tissue.

SUMMARY

Thus, in accordance with the present disclosure, there is provided a method of treating a temozolomide-resistant glioma in a subject comprising administering to said subject a dose of 2,4-disulfonyl phenyl tert-butyl nitrone (2,4-ds-PBN) effective to inhibit the vascularization, growth or spread of said glioma. Administration may be through a route requiring subsequent passage of 2,4-ds-PBN across the blood brain barrier, such as enteral, intravenous, or intra-arterial.

The subject may have a recurrent or metastatic glioma, and or may have previously failed one or more anti-glioma therapies. The effective dose of 2,4-ds-PBN may be from about 5 to about 150 mg/kg body weight per day. The enteral administration may be through dietary supplementation of a food component, or the enteral administration may be in the form of a pill or a liquid. The subject may be a human.

The method may further comprise a secondary anti-glioma therapy, such as radiation, surgery, or chemotherapy, such as temozolomide, lomustine, vincristine, matulane, PCV, BCNU, CCNU and/or DFMO. The secondary anti-glioma agent may be temozolomide, and the effective dose of temozolomide may be lower than the standard monotherapy dose of temozolomide.

The effective amount of 2,4-ds-PBN may be from about 0.005 w/w % to about 0.1 w/w % of the diet being administered. The glioma may be an astrocytoma, an oligodendroglioma, or a glioblastoma multiforme, or a TGF-β1-, MGMT- and/or APGN-expressing form of any of the foregoing.

The method may further comprise assessing therapeutic efficacy by measuring the expression of liposaccharide binding protein prior to and after a treatment with 2,4-ds-PBN. The method may further comprise assessing expression of LBP, wherein reduced LBP levels as compared to untreated controls indicates improved prognosis.

In another embodiment, there is provided a method for inhibiting of development of glioma temozolomide resistance in a subject comprising (a) identifying a subject having a glioma and (b) administering to said subject doses of (i) 2,4-disulfonyl phenyl tert-butyl nitrone (2,4-ds-PBN), and (ii) temozolomide effective to inhibit the development of temozolomide resistance in said glioma. Administration may be through a route requiring subsequent passage of 2,4-ds-PBN across the blood brain barrier, such as enteral, intravenous, or intra-arterial.

The subject may have a recurrent or metastatic glioma, and or may have previously failed one or more anti-glioma therapies. The effective dose of 2,4-ds-PBN may be from about 5 to about 150 mg/kg body weight per day. The enteral administration may be through dietary supplementation of a food component, or the enteral administration may be in the form of a pill or a liquid. The subject may be a human.

The method may further comprise a secondary anti-glioma therapy, such as radiation, surgery, or chemotherapy, such as temozolomide, lomustine, vincristine, matulane, PCV, BCNU, CCNU and/or DFMO. The secondary anti-glioma agent may be temozolomide, and the effective dose of temozolomide may be lower than the standard monotherapy dose of temozolomide.

The effective amount of 2,4-ds-PBN may be from about 0.005 w/w % to about 0.1 w/w % of the diet being administered. The glioma may be an astrocytoma, an oligodendroglioma, or a glioblastoma multiforme, or a TGF-β1-, MGMT- and/or APGN-expressing form of any of the foregoing. The method may further comprise assessing expression of LBP, wherein reduced LBP levels as compared to untreated controls indicates improved prognosis.

In still another embodiment, there is provided a method for inhibiting glioma recurrence comprising (a) identifying a subject having a glioma and (b) administering to said subject doses of (i) 2,4-disulfonyl phenyl tert-butyl nitrone (2,4-ds-PBN), and (ii) temozolomide effective to inhibit the recurrence of said glioma. Administration may be through a route requiring subsequent passage of 2,4-ds-PBN across the blood brain barrier, such as enteral, intravenous, or intra-arterial.

The subject may have a recurrent or metastatic glioma, and or may have previously failed one or more anti-glioma therapies. The effective dose of 2,4-ds-PBN may be from about 5 to about 150 mg/kg body weight per day. The enteral administration may be through dietary supplementation of a food component, or the enteral administration may be in the form of a pill or a liquid. The subject may be a human.

The method may further comprise a secondary anti-glioma therapy, such as radiation, surgery, or chemotherapy, such as temozolomide, lomustine, vincristine, matulane, PCV, BCNU, CCNU and/or DFMO. The secondary anti-glioma agent may be temozolomide, and the effective dose of temozolomide may be lower than the standard monotherapy dose of temozolomide.

The effective amount of 2,4-ds-PBN may be from about 0.005 w/w % to about 0.1 w/w % of the diet being administered. The glioma may be an astrocytoma, an oligodendroglioma, or a glioblastoma multiforme, or a TGF-β1-, MGMT- and/or APGN-expressing form of any of the foregoing. The method may further comprise screening for glioma formation in said subject. The method may further comprise assessing efficacy by measuring the expression of liposaccharide binding protein prior to and after a treatment with 2,4-ds-PBN. The method may further comprise assessing expression of LBP, wherein reduced LBP levels as compared to untreated controls indicates improved prognosis.

In still yet another embodiment, there is provided a method of detecting glioblastoma comprising (a) obtaining a sample from a subject; and (b) assessing liposaccharide binding protein (LBP) level in said sample, wherein an LBP level higher than that from a comparable normal control sample indicates the presence of glioblastoma in said subject. Assessing LBP level may comprise immunologic assessment or nucleic acid assessment, such as immunologic assessment selected from ELISA, RIA, Western blot, or immunohistochemistry, or nucleic acid assessment selected from RT-PCR, Northern blot, RNA-Seq or microarray. The sample may be whole blood, serum, plasma or urine.

A further embodiment comprises a method of monitoring glioblastoma progression comprising (a) obtaining a sample from a subject; (b) assessing liposaccharide binding protein (LBP) level in said sample; and (c) repeating steps (a) and (b) at a second time point, wherein an LBP level higher in step (c) as compared to step (b) indicates progression of glioblastoma in said subject. Assessing LBP level may comprise immunologic assessment or nucleic acid assessment, such as immunologic assessment selected from ELISA, RIA, Western blot, or immunohistochemistry, or nucleic acid assessment selected from RT-PCR, Northern blot, RNA-Seq or microarray. The sample may be whole blood, serum, plasma or urine.

Yet a further embodiment comprises a method of staging glioblastoma comprising (a) obtaining a sample from a subject; (b) assessing liposaccharide binding protein (LBP) level in said sample; (c) comparing the LBP level of step (b) with a control samples for low, mid and/or high grade glioblastomas, and (d) assigning a grade to said glioblastoma in said subject. Assessing LBP level may comprise immunologic assessment or nucleic acid assessment, such as immunologic assessment selected from ELISA, RIA, Western blot, or immunohistochemistry, or nucleic acid assessment selected from RT-PCR, Northern blot, RNA-Seq or microarray. The sample may be whole blood, serum, plasma or urine.

An additional embodiment comprises a method of treating a subject with glioblastoma comprising administering to said subject a therapeutic agent linked to a liposaccharide binding protein (LBP) targeting agent. The LBP targeting agent may be an antibody, ScFv, Fab or F(ab')$_2$ or peptide. The therapeutic agent may be a chemotherapeutic agent, a radiotherapeutic agent, immunotherapeutic agent or biological agent. The chemotherapeutic agent may be temozolomide or 2,4-disulfonyl phenyl tert-butyl nitrone (2,4-ds-PBN). The glioblastoma may be drug resistant, such as temozolomide resistant. The glioblastoma may have been treated previously with temozolomide and/or 2,4-disulfonyl phenyl tert-butyl nitrone (2,4-ds-PBN). The glioblastoma may be recurrent and/or metastatic. The linkage of the therapeutic agent to LBP may be cleavable. The method may further comprise assessing LBP expression in said patient or said glioblastoma.

Yet an additional embodiment comprises a method of identifying a glioblastoma boundary in a subject comprising (a) administering to said subject an imaging agent linked to liposaccharide binding protein; and (b) imaging a glioblastoma site in said subject. The method may further comprise administering to said subject an imaging agent linked to ELTD1, Slit-3 or Spondin-1. The imaging agent may be a dye, a radiolabel, a fluorescent label, a chemiluminescent label, an MRI label or a near infrared label. The method may further comprise excising said glioblastoma following imaging, optionally further comprising re-imaging said glioblastoma site after excising.

An even further embodiment comprises a method of identifying a glioblastoma cell in a tissue sample from a subject comprising (a) obtaining a tissue sample from said subject (b) contacting said tissue sample with a label linked to liposaccharide binding protein; and (c) detecting said label-LBP conjugate bound to said tissue sample. The method may further comprising contacting said tissue sample with a label linked to said subject an imagine agent linked to ELTD1, Slit-3 or Spondin-1. The label may be a dye, a radiolabel, a fluorescent label, a chemiluminescent label, an MRI label or a near infrared label. The tissue sample may be an unfixed fresh biopsy sample. The tissue sample may be a fixed biopsy sample.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device or a method that "comprises," "has," "contains," or "includes" one or more elements possesses those one or more elements, but is not limited to possessing only those one or more elements or steps. Likewise, an element of a device or method that "comprises," "has," "contains," or "includes" one or more features possesses those one or more features, but is not limited to possessing only those one or more features.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8: In vitro IC50 assessment of TMZ-resistant (T98G, G55) and TMZ-sensitive (U251) GBM cell lines combined with OKN-007.

FIGS. 11A-C: LBP levels by tumor grade. LBP level is elevated in high-grade human patient gliomas compared with tumors classified as low-grade gliomas. Representative immunohistochemistry staining for LBP in high-grade glioma: glioblastoma multiforme (FIG. 11A), and in low-grade astrocytoma (FIG. 11B). (FIG. 11C) Immunohistochemistry (IHC) score means of LBP expression in high-grade (GBM-glioblastomas, AA-anaplastic astrocytomas, AO-anaplastic oligodendrogliomas; 94 patient tissue samples) and low-grade (LGA-low grade astrocytomas, oligo-benign oligodendrogliomas; 45 patient tissue samples) human gliomas. Grading criteria: 0: 0%; 1: 0 to <25%; 2: 25 to <50%; 3: 50 to <75%; 4: 75-100% detection of IHC stain.

(FIG. 13A) Percent animal survival Kaplan-Meier curve for untreated (UT), and TMZ-, OKN-007 and combined OKN-007 and TMZ-treated G55 glioma-bearing mice. All treatment groups were found to have a significantly higher survival ($p<0.05$ or more), compared to UT G55-glioma-bearing mice. The combined treatment group was found to have a significantly higher percent survival ($p<0.01$) than the TMZ-treated group. (FIG. 13B) In vivo tumor volumes ($mm^3$) obtained at days 19-22 following MRI detection of tumors ($>5$ $mm^3$). All treatment groups were found to have significantly lower tumor volumes ($p<0.01$ or more), compared to the UT group.

FIGS. 21A-C: TGFβ1 IHC of rat F98 orthotopic tumors (mid-tumor region) either (FIG. 21A) untreated, or (FIG. 21B) treated with OKN-007. (FIG. 21C) ELISA TGFβ1 protein levels (pg/mL) in untreated (UT) or OKN-007 (OKN)-treated from F98 tumor tissue lysates.

DESCRIPTION OF ILLUSTRATIVE EMBODIMENTS

Figure 1:
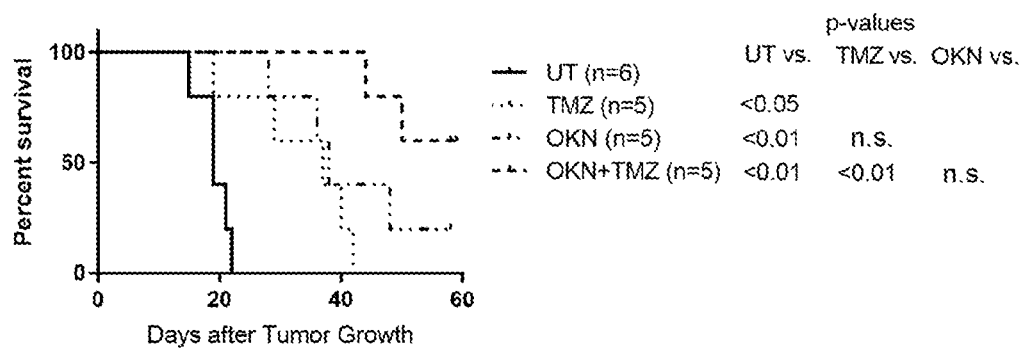
FIG. 1: Percent animal survival Kaplan-Meier curve for untreated, and TMZ-, OKN-007 and combined OKN-007 and TMZ-treated G55 glioma-bearing mice.

The prognosis of patients who are diagnosed with glioblastoma multiforme is very poor, due to the difficulty of an early and accurate diagnosis and the lack of currently efficient therapeutic compounds. In addition, gliomas that are initially sensitive to drugs can become resistant over time, thereby presenting an additional challenge to treating this highly lethal form of cancer.

As mentioned above, 2,4-ds-PBN, a structural analog of PBN, was able to decrease tumor volumes and the delay in tumor growth rate of animals with gliomas, and also significantly increased survival rate. However, it is unknown whether 2,4-ds-PBN could positively affect the outcome of temozolomide (TMZ)-based therapies, including prevention and overcoming of TMZ-resistance in glioma cells. Given the standard-of-care status of TMZ treatment, and the prevalence of TMZ resistance, such a benefit this would be of considerable significance to patients undergoing treatment with TMZ.

Thus, the inventor sought to look at the effects of 2,4-ds-PBN in the context of TMZ resistance and co-therapy. In vitro cell data clearly indicates that 2,4-ds-PBN significantly decreases the cell viability of TMZ-resistant GBM cells treated with TMZ. The in vivo data clearly shows that combined 2,4-ds-PBN and TMZ treatment substantially increases animal survival and decreases tumor volumes in a TMZ-resistant glioma xenograft nude mouse model. These unexpected results point towards the combined use of 2,4-ds-PBN and TMZ as a powerful new therapeutic regimen for gliomas.

2. ANAPLASTIC GLIOMA STRATA

A. Clinical Features

The anaplastic gliomas are intermediate grade infiltrative gliomas—classified between low (localized, slow growing) and glioblastoma multiforme (rapidly growing and highly invasive). Anaplastic astrocytomas (AA) are tumors that arise from brain cells called astrocytes and/or their precursors. Astrocytes are support cells of the central nervous system. The majority of astrocytic tumors in children are low-grade, whereas the majority in adults are high-grade. These tumors can occur anywhere in the brain and spinal cord.

Oligodendrogliomas are gliomas derived from oligodendrocytes and/or their precursors. Oligodendrocytes that have a role in the structure and function of myelinated neurons in the brain. Anaplastic oligodendroglioma (AO) are more aggressive than oligodendrogliomas, but are also more sensitive to chemotherapy than are anaplastic astrocytomas. A high rate of response to the use of PCV (procarbazine, CCNU, vincristine) chemotherapy has led to the common use of PCV chemotherapy prior to radiation therapy, following irradiation, and/or at tumor recurrence and progression. Another glioma appears as histologic mixture of both oligodendroglioma and astrocytoma tumor forms and is called oligoastrocytoma. While oligoastrocytoma can be low-grade, the majority of the mixed oligoastrocytomas are anaplastic oligoastrocytomas (AOA).

The last glioma subgroup are ependymomas. One subtype of malignant ependymomas is the anaplastic ependymoma (AE); these tumors arise from ependymal cells and/or their precursors that line the cerebrospinal fluid passageways, called ventricles. These tumors are classified as either supratentorial (in the top part of the head) or infratentorial (in the back of the head).

Clinical features and symptoms produced by gliomas depend on the location of the tumor and the age of the patient. The most common location for gliomas is in the cerebral hemispheres in adults and the cerebellum, brainstem, hypothalamus, and thalamus in children.

Spinal cord gliomas are much less common then gliomas of the brain. Patients with these tumors have symptoms that vary depending on location in the brain or spinal cord. They can produce symptoms of headache, seizures, nausea and vomiting, limb weakness, unilateral sensory changes, personality change, and unsteadiness in walking.

B. Classifications

Anaplastic Astrocytoma. The histologic features of anaplastic astrocytomas are similar to those of low-grade astrocytomas but these features are more abundant and exaggerated. These tumors are WHO grade III (Kleihues et al., 1993; Kleihues and Cavenee, 2000). Cellularity is more increased, as are nuclear and cellular pleomorphism. These features may be extreme, with back-to-back cells and bizarre, hyperchromatic nuclei. Cytoplasm may be scanty, with nuclear lobation and enlargement indicating anaplasia. Mitotic activity is easily recognized in most anaplastic astrocytomas but inexplicably may be absent in areas with gemistocytes.

The range of anaplasia in this grade is broad, with some examples showing low cellularity and pleomorphism with a few mitotic figures and others being highly cellular and pleomorphic with frequent mitoses, lacking only the necrosis required for a histologic diagnosis of glioblastoma. For this reason, it is useful to have a more objective indicator of behavior, and some markers of cell proliferation have been used in an attempt to predict prognosis more accurately. The most used markers in this area have been antibodies to bromodeoxyuridine (BrdU) and Ki-67 (Davis et al., 1995). The cellular incorporation of BrdU is a specific marker of the DNA synthesis phase of the cell cycle, whereas the Ki-67 antibody labels an antigen that is present in all phases of the cell cycle except Go. Both antibodies can be identified by immunohistochemical staining in paraffin-embedded tissue sections. As a generalization, higher labeling rates for anaplastic astrocytomas is associated with poor prognosis (Hoshino et al., 1993; Davis et al., 1995; Lamborn et al., 1999).

Glioblastoma multiforme. Glioblastoma, also known as glioblastoma multiforme, is the glioma with the highest grade of malignancy, WHO grade IV (Kleihues and Cavenee, 2000). It represents 15% to 23% of intracranial tumors and about 50%-60% of astrocytomas. Most examples are generally considered to arise from astrocytes because glial fibrillary acidic protein can be identified in the cell cytoplasm. Some examples, however, apparently arise from other glial lineages, such as oligodendrocytes. Glioblastoma is the most frequently occurring astrocytoma. Autopsy and serial biopsy studies have shown that some astrocytomas progress through the grades of malignancy with transformation from low-grade to anaplastic astrocytoma to glioblastoma (Muller et al., 1977). But, because some examples of glioblastoma appear to arise rapidly in otherwise normal patients and are recognized when they are small, it is thought that this variety of glioblastoma can also arise directly from malignant transformation of astrocyte precursor cells without passing through the lower grades of malignancy (Kleihues and Ohgaki, 1997; 1999).

Tumor necrosis is the characteristic gross feature that distinguishes glioblastoma from anaplastic astrocytoma (Nelson et al., 1983; Burger et al., 1985; 1991). Another microscopic feature that is distinctive and diagnostic is the presence of proliferative vascular changes within the tumor. These changes may occur in the endothelial cells (vascular endothelial hyperplasia or proliferation) or in the cells of the vessel wall itself (vascular mural cell proliferation). Both types of change are sometimes considered together as microvascular proliferation. Glioblastomas cellularity is usually extremely high. The individual cells may be small, with a high nuclear:cytoplasmic ratio, or very large and bizarre, with abundant eosinophilic cytoplasm. These same small cells may appear to condense in rows around areas of tumor necrosis, forming the characteristic pseudopalisades. Glioblastoma tumors have a propensity to infiltrate the brain extensively, spreading even to distant locations and giving the appearance of a multifocal glioma. Some examples are truly multifocal (i.e., arising in multiple simultaneous primary sites) while many of these multifocal tumors show a histologic connection when the whole brain is examined at autopsy.

Oligodendrogliomas. Like astrocytomas, oligodendrogliomas mimic the histology of their presumed cell of origin. They also arise primarily in the white matter but tend to infiltrate the cerebral cortex more than do astrocytomas of a similar grade of malignancy. Like astrocytomas, grading schemes of histologic malignancy have been used for oligodendrogliomas, but these correlate less well with prognosis than those used for astrocytomas (Burger et al., 1987; Bigner et al., 1998; Daumas-Duport et al., 1997). Many of the histologic features used to grade oligodendrogliomas are similar to those used for astrocytomas: cellularity, pleomorphism, mitotic activity, vascular changes, and necrosis. Lower-grade oligodendrogliomas may have microcysts. Oligodendrogliomas of all histologic grades tend to infiltrate the cortex readily and to form clusters of neoplastic cells in the subpial region, around neurons, and around blood vessels. In general, the cells of oligodendrogliomas have round, regular nuclei and distinct cytoplasmic borders with clearing of the cytoplasm. Another fairly distinctive and diagnostically helpful feature is the vascular pattern of oligodendrogliomas, referred to as "chicken-wire" vessels that can divide the tumor into discrete lobules. With increasing anaplasia, oligodendrogliomas can become highly cellular and pleomorphic, approaching an appearance of glioblastoma multiforme with the presence of necrosis. Although it is correct to classify these as anaplastic oligodendrogliomas, some would use the term glioblastoma once necrosis is identified in any high-grade glial neoplasm. One justification for separating anaplastic oliogdendrogliomas from astrocytic glioblastomas is the slightly better prognosis of the former, even in this highest grade of malignancy. Some authors have reported that a MIB-1 labeling index of >3%-5% predicts a worse prognosis in oligodendrogliomas (Heegard et al., 1995; Kros et al., 1996; Dehghani et al., 1998).

Oligoastrocytomas. Many, if not most, oligodendrogliomas occur with a regional or intimate cellular mixture of astrocytoma. For the diagnosis of mixed glioma, the proportion of each should be substantial, but authors have differing opinions with respect to exact numbers;

usually a mixture with a range from 10% to 25% of the minor element is used to diagnose a mixed glioma. Oligoastrocytomas and anaplastic oligoastrocytomas correspond to WHO grade II or grade III, respectively (Kleihues and Cavenee, 2000). Histologic features of anaplasia may be present in either component and will affect the prognosis adversely. Such features include marked cellular pleomorphism, high cellularity, and a high mitotic rate. Microvascular proliferation and necrosis may also be seen. Prognosis and response to therapy have not been shown to depend on the proportion of the oligodendroglial versus the astrocytic component (Shaw et al., 1994), although paradoxically, the BrdU LI of the oligodendroglial component is more predictive for survival than the astrocytic component (Wacker et al., 1994) and far advanced tumor progressions are dominated by the astrocytic component.

3. PHENYL N-TERT-BUTYL NITRONES (PBNS) AND TEMOZOLOMIDE (TMZ)

A. PBN's

The compound phenyl N-tert-butyl nitrone (PBN) was first synthesized in the 1950's, but in 1968 it was discovered to be very useful to trap and stabilize free radicals in chemical reactions and hence it was termed a spin-trap (Janzen, 1971). Although PBN is the prototype spin-trap, several other nitrones have been synthesized and found useful to trap and characterize free radicals in chemical reactions. These spin traps were used in chemical reactions first, but in the mid-1970's they began to be used to trap free radicals in biochemical and biological systems (Poyer et al., 1978). Pharmacokinetic studies have shown that PBN is readily and rapidly distributed almost equally to all tissues, has a half-life in rats of about 132 minutes and is eliminated mostly in the urine. Relatively few metabolism studies have been done, but it is known that some ring hydroxylation (primarily in the para position) of the compound occurs in the liver.

Novelli first showed that PBN could be used to protect experimental animals from septic shock (Novelli et al., 1986), and indeed this was later confirmed by other groups (Pogrebniak et al., 1992). The use of PBN and derivations as pharmacological agents began after discoveries in 1988 that showed that PBN had neuroprotective activity in experimental brain stroke models (Floyd, 1990; Floyd et al., 1996; Carney et al., 1991). These results were repeated and extended, (see Clough-Helfman et al., 1991; Cao et al., 1994; Folbergrova et al., 1995; Pahlmark et al., 1996). Others have summarized the extensive neuroprotective pharmacological research effort on PBN and derivatives (Floyd, 1997; Hensley et al., 1996). In addition to neurodegenerative diseases, PBN has been shown to protect in other pathological conditions where ROS-mediated processes are involved, including diabetes and many other conditions. The mechanistic basis of why PBN and some of its derivatives are so neuroprotective in experimental stroke and several other neurodegenerative models has not been completely elucidated yet. However, it is clear that its action cannot simply be explained by its ability to trap free radicals.

The general formula for PBNs is:

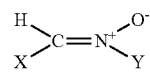

wherein:
X is phenyl or

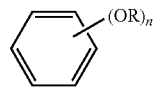

R is H,

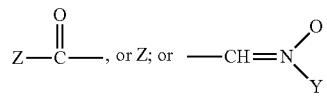

and n is a whole integer from 1 to 5; or

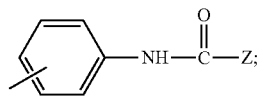

Y is a tert-butyl group that can be hydroxylated or acetylated on one or more positions; phenyl; or

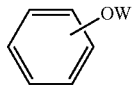

wherein W is

or Z; and Z is a $C_1$ to $C_5$ straight or branched alkyl group.

B. PBN's in Cancer

U.S. Pat. No. 5,569,902 (incorporated herein by reference) describes the use of nitrone free radical trapping agents for the treatment of cancer. Specifically, PBN and related compounds are described as being useful in the preparation of an anti-carcinogenic diet and the preparation of such supplemented diets. Those subjects most likely to beneficially receive the nitrones would include: (1) those having had pretumor tests indicating a high probability of the presence of tumors, (2) those exposed to very potent carcinogenic environments and their probability of tumor progression is high, and (3) to those whose genetic predisposition makes their likelihood of tumor development high.

U.S. Patent Publication 2007/0032453 (incorporated herein by reference) describes the effect of the anti-inflammatory phenyl N-tert-butyl nitrones (PBNs) on gliomas using MRI techniques. PBN itself was able to control tumor development when provided to a subject either before, at the time of or after tumor implantation. Thus, it was proposed to use PBN, and related nitrone free radical trapping agents, as therapeutic agents for gliomas.

C. 2,4-Disulfonyl Phenyl N-Tert-Butyl Nitrone (2,4-ds-PBN)

U.S. Pat. No. 5,488,145 (incorporated herein by reference) describes 2,4-disulfonyl phenyl-tert-butyl nitrone and its pharmaceutically acceptable salts. These materials were described as useful pharmaceutical agents for oral or intravenous administration to patients suffering from acute central nervous system oxidation as occurs in a stroke or from gradual central nervous system oxidation which can exhibit itself as progressive central nervous system function loss.

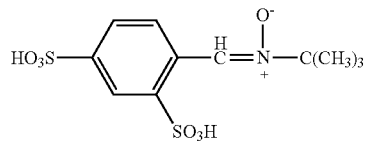

2,4-disulfonyl PBN (also referred to as OKN-0007)

2,4-disulfonyl PBN's two sulfonate groups was expected to exhibit improved water solubility, but was also expected to exhibit poor transport across the blood/brain barrier because of its lipophobic character. However, when the present compound was made and tested in vivo, it showed an unexpected increase in efficacy as compared to PBN. This increase in efficacy occurred along with an increase in potency as compared to PBN. In direct contrast to this marked increase in potency and efficacy there was a marked and highly significant decrease in toxicity as compared to PBN.

These results were unexpected because in the general literature on structure/activity relationships within specific defined families of compounds therapeutic potency typically covaries with toxicity. Thus, most related compounds maintain their ratio of therapeutic potency to toxicity. In contrast, the compound of this invention deviates from this expected relationship when its potency increased and its toxicity decreased relative to closely related analogs.

Accordingly, in one aspect, the invention provides the PBN-disulfonyl compound and its pharmaceutically acceptable salts. In a second aspect, the invention provides intravenously- and orally-administrable pharmaceutical compositions having this compound or its salt as active ingredient.

2,4-ds PBN may exists at higher pHs in an ionized salt form:

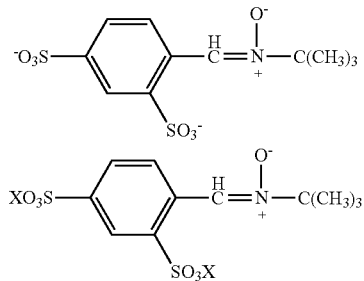

or where X is a pharmaceutically acceptable cation. Most commonly, this cation is a monovalent material such as sodium, potassium or ammonium, but it can also be a multivalent alone or cation in combination with a pharmaceutically acceptable monovalent anion, for example calcium with a chloride, bromide, iodide, hydroxyl, nitrate, sulfonate, acetate, tartrate, oxalate, succinate, palmoate or the like anion; magnesium with such anions; zinc with such anions or the like. When these combinations of a polyvalent cation and a monovalent anion are illustrated in structural formulae, herein, the monovalent anion is identified as "Y."

Among these materials, the free acid and the simple sodium, potassium or ammonium salts are most preferred with the calcium and magnesium salts also being preferred but somewhat less so.

2,4-ds PBN can be prepared by a two-step reaction sequence. In the first step, commercially available tertiary butyl nitrate (2-methyl-2-nitropropane) is converted to the corresponding n-hydroxyl amine using a suitable catalyst such as an activated zinc/acetic acid catalyst or an aluminum/mercury amalgam catalyst. This reaction can be carried out in 0.5 to 12 hours and especially about 2 to 6 hours or so at a temperature of about 15-100° C. in a liquid reaction medium such as alcohol/water mixture in the case of the zinc catalyst or an ether/water mixture in the case of the aluminum amalgam catalyst.

In the second step, the freshly formed hydroxylamine is reacted with 4-formyl-1,3-benzenedisulfonic acid, typically with a slight excess of the amine being used. This reaction can be carried out at similar temperature conditions. This reaction is generally complete in 10 to 24 hours. The product so formed is the free acid and is characterized by a molecular weight of 89 g/mole. It is a white powdery material which decomposes upon heating. It is characterized by a solubility in water of greater than 1 gram/ml and a $^1$H NMR spectrum in $D_2O$ of 8.048 ppm (dd, 8.4, 1.7 Hz); 8.836 ppm (d, 8.4 Hz); 8.839 ppm (d, 1.7 Hz); 8.774 ppm (s).

The various salts can be easily formed by admixing the free acid in aqueous medium with two equivalents of the appropriate base, for example, KOH for the potassium salt, and the like.

One synthesis is based on the work by R. H. Hinton and E. G. Janzen (J. Org. Chem. 57:2646-2651, 1992). It involves the condensation of an aldehyde with a hydroxylamine. The hydroxylamine is unstable and is prepared fresh on the day of use using an activated zinc catalyst. The synthesis is as follows.

TABLE 1

Prerequisite Chemicals 1. 95% Ethanol
2. 2-Methyl-2-nitropropane
3. Zinc dust
4. Glacial acetic acid
5. Diethyl ether
6. Saturated sodium chloride
7. Magnesium Sulfate, Anhydrous solid
8. 4-Formyl-l,3-benzenesulfonic acid (MW 310.21 g/mole), disodium salt, hydrate
9. Methanol
10. Dichloromethane

TABLE 2

Preparation of N-t-Butylhydroxylamine

1. A 500 mL three neck round bottom flask is equipped with a magnetic stir bar, thermometer adapter, thermometer, and addition funnel.
2. 95% ethanol (350 mL) was added to the flask and cooled to 10° C. in an ice bath.
3. 2-Methyl-2-nitropropane (6.18 g, 0,060 mole), and zinc dust (5.89 g, 0,090 mole) were added in single portions.
4. Glacial acetic acid (10.8 g, 0, 180 mole) was placed in the addition funnel and added dropwise at such a rate with vigorous stirring to maintain the temperature below 15° C.
5. The ice bath was removed and mixture was stirred for 3 hrs at room temperature.
6. The solvent was stripped from the mixture, leaving t-butylhydroxylamine, zinc acetate, and water.
7. Dichloromethane (50 mL) was added and the mixture filtered through a Buchner funnel.
8. The zinc acetate cake left on the filter paper was washed with 2X 25 mL dichloromethane.
9. Water was separated from the filtrate in a separatory funnel and the organic layer dried over magnesium sulfate.
10. The magnesium sulfate was removed by filtering through fluted filter paper, then dichloromethane stripped off by rotary evaporation.
11. The product (100% yield = 5.34 g), a viscous liquid, was dissolved in methanol (50 mL) for use below.

TABLE 3

Preparation of 2,4-disulfonylphenyl-N-t-butylnitrone

1. A 3-neck 250 ml round bottom flask was set up with a stir bar, a gas dispersion tube, an addition funnel, and a Friedrichs condenser cooled with recirculating ice water.
2. To the flask were added 200 mL of methanol, 4-formyl-1,3 -benzenedisulfonic acid (9.31 g, 30 mmoles) and N-t-butylhydroxylamine (25 mL of the methanol solution from part A, 30 mmoles theoretical).
3. The reaction was heated to reflux with a heating mantle while bubbling the reaction with nitrogen with stirring.
4. The mixture was refluxed for 2 hours.
5. The remainder of hydroxylamine from above was added.
6. Refluxing was continued with nitrogen bubbling for at least 18 hours, but not more than 24 hours.
7. The hot reaction mixture was filtered on a Buchner funnel, and the solid washed with hot methanol.
8. The methanol was stripped off by rotary evaporation to a yellow, viscous oil.
9. Hot 1:1 ethanol:acetone (200 mL) was added and the mixture heated to dissolve the oil.
10. The solution was cooled to crystallize the product.
11. The product was collected on a Buchner funnel and dried under vacuum overnight.
12. The reaction typically gives 75% yield of a white powder.

Other methods of synthesis are disclosed in the prior art as well.

D. Temozolomide

Temozolomide (TMZ; brand names Temodar® and Temodal® and Temcad®) is an oral chemotherapy drug. It is an alkylating agent used as a treatment of some brain cancers; as a second-line treatment for astrocytoma and a first-line treatment for glioblastoma multiforme. TMZ is a prodrug and an imidazotetrazine derivative of the alkylating agent dacarbazine. Its approved indications include nitrosourea- and procarbazine-refractory anaplastic astrocytoma, and newly diagnosed glioblastoma multiforme. TMZ has been available in the U.S. since August 1999, and in other countries since the early 2000s.

The most common side effect from TMZ is bone marrow suppression. The most common non-hematological adverse effects associated with temozolomide are nausea and vomiting, which are either self-limiting or readily controlled with standard antiemetic therapy. These latter effects are usually mild to moderate (grade 1 to 2). The incidence of severe nausea and vomiting is around 4% each. Patients who have pre-existing or a history of severe vomiting may require antiemetic therapy before initiating temozolomide treatment. Temozolomide should be administered in the fasting state, at least one hour before a meal. Antiemetic therapy may be administered before, or following, administration of temozolomide. Temozolomide is contraindicated in patients with hypersensitivity to its components or to dacarbazine. The use of temozolomide is not recommended in patients with severe myelosuppression. A standard oral dose of temozolomide would be 150 $mg/m^2$ daily, increased to 200 $mg/m^2$ daily for maintenance. Lower levels would be anything below standard dosing, including 125 $mg/m^2$, 100 $mg/m^2$, 75 $mg/m^2$, or 50 $mg/m^2$, for example.

Temozolomide is genotoxic, teratogenic and fetotoxic and should not be used during pregnancy. Lactating women should discontinue nursing while receiving the drug because of the risk of secretion into breast milk. One study indicated that women that have taken temozolomide without concomitant fertility preservation measures achieve pregnancy to a lesser rate later in life, but the study was too small to show statistical significance in the hypothesis that temozolomide would confer a risk of female infertility. In male patients, temozolomide can have genotoxic effects. Men are advised not to father a child during or up to six months after treatment and to seek advice on cryoconservation of sperm prior to treatment, because of the possibility of irreversible infertility due to temozolomide therapy. Very rarely temozolomide can cause acute respiratory failure or liver damage. The therapeutic benefit of temozolomide depends on its ability to alkylate/methylate DNA, which most often occurs at the N-7 or O-6 positions of guanine residues. This methylation damages the DNA and triggers the death of tumor cells. However, some tumor cells are able to repair this type of DNA damage, and therefore diminish the therapeutic efficacy of temozolomide, by expressing a protein $O^6$-alkylguanine DNA alkyltransferase (AGT) encoded in humans by the O-6-methylguanine-DNA methyltransferase (MGMT) gene. In some tumors, epigenetic silencing of the MGMT gene prevents the synthesis of this enzyme, and as a consequence such tumors are more sensitive to killing by temozolomide. Conversely, the presence of AGT protein in brain tumors predicts poor response to temozolomide and these patients receive little benefit from chemotherapy with temozolomide.

Laboratory studies and clinical trials have investigated the possibility of increasing the anticancer potency of temozolomide by combining it with other pharmacologic agents. For example, clinical trials have indicated that the addition of chloroquine might be beneficial for the treatment of glioma patients. Laboratory studies found that temozolomide killed brain tumor cells more efficiently when epigallocatechin gallate (EGCG), a component of green tea, was added; however, the efficacy of this effect has not yet been confirmed in brain-tumor patients. Preclinical studies reported in 2010 on investigations into the use of the novel oxygen diffusion-enhancing compound trans sodium crocetinate (TSC) when combined with temozolomide and radiation therapy and a clinical trial was underway as of August 2015.

While the above-mentioned approaches have investigated whether the combination of temozolomide with other agents might improve therapeutic outcome, efforts have also started to study whether altering the temozolomide molecule itself can increase its activity. One such approach permanently fused perillyl alcohol, a natural compound with demonstrated therapeutic activity in brain cancer patients, to the temozolomide molecule. The resultant novel compound, called NEO212 or TMZ-POH, revealed anticancer activity that was significantly greater than that of either of its two parent molecules, temozolomide and perillyl alcohol. Although, as of 2016, NEO212 has not been tested in humans, it has shown superior cancer therapeutic activity in animal models of glioma, melanoma, and brain metastasis of triple-negative breast cancer.

Because tumor cells that express the MGMT gene are more resistant to the effects of temozolomide, researchers investigated whether the inclusion of $O^6$-benzylguanine ($O^6$-BG), an AGT inhibitor, could overcome this resistance and improve the drug's therapeutic effectiveness. In the laboratory, this combination indeed showed increased temozolomide activity in tumor-cell culture in vitro and in animal models in vivo. However, a recently completed phase-II clinical trial with brain-tumor patients yielded mixed outcomes; while there was some improved therapeutic activity when $O^6$-BG and temozolomide were given to patients with temozolomide-resistant anaplastic glioma, there seemed to be no significant restoration of temozolomide sensitivity in patients with temozolomide-resistant glioblastoma multiforme.

4. COMBINATION TREATMENTS

In one embodiment, a 2,4-ds-PBN therapy (optionally including TMZ) may be used in conjunction with another glioma therapy, such as radiation, PCV, DFMO, CCNU or BCNU. These compositions would be provided in a combined amount effective to kill or inhibit proliferation of the cell. This process may involve contacting the cells with the agents at the same time. This may be achieved by contacting the cell with a single composition or pharmacological formulation that includes both agents, or by contacting the cell with two distinct compositions or formulations, at the same time, wherein one composition includes 2,4-ds-PBN and the other includes the second agent.

Alternatively, the 2,4-ds-PBN therapy may precede or follow the other agent treatment by intervals ranging from minutes to weeks. In embodiments where the other agent and 2,4-ds-PBN are applied separately to the cell, tissue or organism, one would generally ensure that a significant period of time did not expire between the time of each delivery, such that the agents would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Multiple administrations of each agent are contemplated. For example, where the 2,4-ds-PBN therapy (optionally including TMZ or other AGT inhibitor) is "A" and the secondary agent or therapy is "B," the following are contemplated:

| A/B/A | B/A/B | B/B/A | A/A/B | A/B/B | B/A/A | A/B/B/B | B/A/B/B |
|---|---|---|---|---|---|---|---|
| B/B/B/A | | B/B/A/B | A/A/B/B | | A/B/A/B | A/B/B/A | B/B/A/A | |
| B/A/B/A | | B/A/A/B | A/A/A/B | | B/A/A/A | A/B/A/A | A/A/B/A | |

Patients will be evaluated for neurological changes considered to be independent of tumor and graded using NCI Common Toxicity Criteria (neurotoxicity). Aside from baseline audiometric testing, repeat audiometric testing for ototoxicity is performed at the physician's discretion for patients who had evidence of hearing loss or progression of hearing loss by neurological examination. In addition, blood counts are performed biweekly, and serum creatinine, alkaline phosphatase, bilirubin and alanine amino-transferase tests are performed before each cycle. Doses may be modified during the course of treatment, primarily based on neutrophil and platelet counts (vincristine, lomustine and matulane) or ototoxicity (DFMO). Occasionally, DFMO dose reductions are required for diarrhea.

A. PCV

PCV is a drug combination therapy employing three different agents—a hydrazine derivative, matulane, a nitrosourea, lomustine, and a tubulin interactive agent, vincristine. It has been used in a number of clinical trials, most notably by the inventor in assessing its effect on high-grade glioma and medulloblastoma tumors. The major side-effect observed with PCV was dose-limiting myelotoxicity. Each of the components of PCV is described below.

It should be noted that the present invention could include the use of BCNU rather than of CCNU (lomustine) since both are nitrosoureas. It also is contemplated that one could use CCNU and procarbazine or BCNU and procarbazine, without vincristine, since vincristine is usually considered to be the least active of the drugs in the PCV combination.

Both hydrazines and nitrosoureas are alkylating agents. As a group, alkylating agents form covalent chemical adducts with cellular DNA, RNA and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. In addition to hydrazine and nitrosoureas, alkylating agents include: triazenes such as dacarabzine and temozolomide, nitrogen mustards such as chlorambucil, cyclophosphamide, isofamide, mechlorethamine, melphalan, uracil mustard; aziridine such as thiotepa; methanesulphonate esters such as busulfan; platinum complexes such as cisplatin, carboplatin; bioreductive alkylators, such as mitomycin and altretemine. Any of these compounds may be used together or individually, in combination with the compounds of the present invention.

i. Hydrazine and Triazene Derivatives

Hydrazine and triazene derivatives are similar to nitrosoureas in that they decompose spontaneously or are metabolized to produce alkyl carbonium ions, which alkylate DNA. This class of compounds includes matulane, dacarbazine and temozolomide.

The active ingredient in matulane is Procarbazine Hydrochloride (N-isopropl-alpha-(2-methylhydrazino)-p-toluamide monohydrochloride). It is available from Roche Laboratories, Inc. It was approved in 1969 for treatment of Hodgkins' Disease. The typical form is an oral capsule that contains 50 mg procarbazine as the hydrochloride. Dosages vary depending upon whether procarbazine is being used as a combination drug with other anticancer drugs or as a single therapeutic agent. A suggested guideline per the PDR for single agent use is 100 mg two times daily for 14 days.

The exact mode of actions of matulane is not clear. There is some evidence that the drug acts by inhibition of protein, RNA and DNA synthesis. It is primarily metabolized in the liver and kidneys and appears to be auto-oxidized to the azo derivative with the release of hydrogen peroxide. The azo derivative isomerizes to the hydrazone and, following hydrolysis, splits into a benzylaldehyde derivative and methylhydrazine. The methylhydrazine is further degraded to $CO_2$ and $CH_4$, and possibly hydrazine, whereas the aldehyde is oxidized to acid which is excreted in the urine.

Matulane exhibits monamine oxidase inhibitory activity (MAOI), so a diet that restricts foods which contain high tyramine content should be followed. Drugs to be avoided during therapy include antihistamines, sympathomimetics, barbiturates, narcotics, hypotensive agents or phenothiazines, and ethyl alcohol. Some foods are also to be avoided during procarbazine such as naturally aged cheeses, chocolates, nuts, and bananas as they could theoretically lead to a hypertensive complication in some patients. Also, unacceptable toxicity may occur if matulane is used in patients with impairment of renal and/or hepatic function. Treatment may be curtailed in the event of central nervous system signs or symptoms such as paresthesias, neuropathies or confusion; neutropenia (absolute neutrophil count under 1500/µl), thrombocytopenia (platelets under 100,000/µl), hypersensitivity reaction, ulceraction or persistent spot of soreness around the oral cavity, diarrhea or loose stools, hemorrhage or bleeding tendencies.

Adverse but expected reactions include leukopenia, neutropenia, anemia, and thrombocytopenia. Commonly reported acute side effects are nausea and vomiting during or shortly after dose administration.

ii. Nitrosoureas

Nitrosoureas represent a group of therapeutic alklyating agents. This class of compounds includes lomustine, carmustine, semustine, steptozocin, and nimustine.

(a) Lomustine

Lomustine is a synthetic alkylating agent, also known as CCNU, with the chemical name of 1-(2-chloroethyl)-3-cyclohexyl-1-nitrosourea. It was approved in 1977 for treatment of brain tumors and Hodgkin's Disease. It is available from Bristol Myers Squibb as oral capsule, available in 10 mg, 40 mg and 100 mg forms. Dosages may vary depending upon whether lomustine is being used as a single agent or in a combination in addition to other chemotherapeutic agents. As a single agent in previously untreated patients, the recommended dosages per the PDR is 130 mg as a single oral dose every 6 weeks. Lomustine crosses the blood brain barrier.

It is believed that CCNU alkylates DNA and RNA. It is cross-resistant with other nitrosoureas and some but not all alkylating agents. It may also inhibit several key enzymatic processes by carbamoylation of amino acids in proteins.

The most common and severe toxic side effects are bone marrow suppression leading to thrombocytopenia and leukopenia, which may contribute to bleeding and infections. Bone marrow toxicity is cumulative and thus dosage adjustments must be considered on the basis of the nadir blood counts from prior doses.

(b) Carmustine

Carmustine, also known as BCNU, with the chemical name of N,N'-Bis(2-chloroethyl)-N-nitrosurea, is a nitrosurea alkylating agent approved by the FDA in 1977. Carmustine has been used for many years for treatment of primary brain tumors and is used for the treatment of gliomas. Carmustine is available from Bristol Meyers Squibb in packages containing vials of 10 mg carmustine and 3 ml sterile diluent for delivered by i.v. injection. As a single agent carmustine is administered at about 150-200 $mg/m^2$ every 6 weeks. In combination regimens, carmustine may be given in does similar to those of lomustine. An alternative mode of delivery is by wafers implanted directly into the tumor site (Gliadel® Wafer).

Potential side effects include bone marrow suppression, anemia, diarrhea, low white blood cell and platelet counts, pulmonary toxicity and swallowing difficulties.

iii. Tubulin Interactive Agents

Tubulin interactive agents interfere with cell division by binding to specific sites on Tubulin, a protein that polymerizes to form cellular microtubules. Microtubules are critical cell structure units. When the interactive agents bind on the protein, the cell cannot properly form microtubules.

Tubulin interactive agents include vincristine and vinblastine, both alkaloids and the taxanes, such as paclitaxel and docetaxel.

Vincristine, is available as Oncovin™ from Eli Lilly & Company and as Vincristine Sulfate from Faulding. Also called vincaleukoblastine, a 22-oxo-, sulfate (1:1) (salt), the salt of an alkaloid obtained from a common flowering herb, the periwinkle plant. It is delivered by intravenous injection. It was approved in 1963 on label for Ewing's Sarcoma, rhabdomyosarcoma, Wilm's Tumor, neuroblastoma, Hodgkin's Disease and leukemia.

The mechanism of action remains under investigation; however, there is an indication that inhibition of microtubule formation in the mitotic spindle, resulting in an arrest of dividing cells at the metaphase state, is involved. The liver is the major excretory organ. Most of an intravenous dose of Vincristine is excreted into the bile after rapid tissue binding. Vincristine does not appear to cross the blood brain barrier.

Vincristine has been reported to reduce blood levels of antiseizure medications and to increase seizure activity. The most common adverse reaction is hair loss. Leukopenia, neuritic pain and constipation occur, but usually for less than 7 days.

B. DFMO

Numerous highly proliferative types of cancer are associated with increased levels of the polyamines putrescine, spermidine, and spermine in tumor tissue and blood and urine of mammals with cancer. Studies have shown that this can be related to increased polyamine synthesis by the rate-limiting enzyme, ornithine decarboxylase (ODC). The pathway for polyamine synthesis begins with L-ornithine. This natural amino acid, although not normally incorporated into proteins, is part of the urea cycle which metabolizes arginine to ornithine and urea. Ornithine is converted by ornithine decarboxylase (ODC) to putrescine and $CO_2$ and is considered to be the rate-limiting step in the production of polyamines. With the addition of propylamine donated from S-adenosylmethionine, putrescine is converted to spermidine. Spermidine is then converted to spermine by spermine synthetase, again in association with the decarboxylation of S-adenosylmethionine. Putrescine, spermidine and spermine represent the three major polyamines in mammalian tissues. Polyamines are found in animal tissues and microorganisms and are known to play an important role in cell growth and proliferation. Although the exact mechanism of the role of the polyamines in cell growth and proliferation is not known, it appears that the polyamines may facilitate macromolecular processes such as DNA, RNA, or protein synthesis. Polyamine levels are known to be high in the testes, ventral prostate, and thymus, in psoriatic skin lesions, and in other cells undergoing rapid growth processes.

It also is well known that the rapid proliferation of tumor tissue is marked by an abnormal elevation of polyamine levels. Hence, the polyamines also may play an important role in the maintenance of tumor growth. Thus, ODC inhibitors, such as DFMO, may exert their therapeutic effect by blocking the formation of the polyamines and thereby slowing, interrupting, or arresting the proliferation and metastases of the tumor tissue.

DFMO (α-difluoromethylornithine, eflornithine, Ornidyl®) is a structural analog of the amino acid L-ornithine and has a chemical formula $C_6H_{12}N_2O_2F_2$. DFMO can be employed in the methods of the invention as a racemic (50/50) mixture of D- and L-enantiomers, or as a mixture of D- and L-isomers where the D-isomer is enriched relative to the L-isomer, for example, 70%, 80%, 90% or more by weight of the D-isomer relative to the L-isomer. The DFMO employed may also be substantially free of the L-enantiomer.

The dose limiting toxic effect of DFMO is thrombocytopenia (abnormally few platelets in the blood), which occurs in about 50% of patients, leukopenia (abnormally few leukocytes), or anemia. This toxic effect is relatively harmless and reversible and cease upon withdrawal of the drug.

The effect of an ODC inhibitor for the control of the growth rate of rapidly proliferating tumor tissue has been assessed in standard animal tumor models. For example, the anti-tumor effect of DFMO has been demonstrated in the following animal tumor models: L1210 leukemia in mice, EMT6 tumor in Balb/C mice, 7,12-dimethylbenzanthracene-induced (DMBA-induced) mammary tumor in rats, and DFMO Morris 7288C or 5123 hepatoma in Buffalo rats. In addition, the anti-tumor effect of DFMO in combination with various cytotoxic agents has been demonstrated as follows: (a) in combination with vindesine or adriamycin in L1210 leukemia in mice, in Morris 7288C hepatoma in Buffalo rats, and in EMT6 tumor in mice, (b) in combination with cytosine arabinoside in L1210 leukemia in mice, (c) in combination with methotrexate in L1210 leukemia in mice, (d) in combination with cyclophosphamide in EMT6 tumor in mice and in DMBA-induced tumor in mice, (e) in combination with BCNU in mouse glioma 26 brain tumor, and (f) in combination with MGBG in L1210 leukemia in mice, in Morris 7288C hepatoma in Buffalo rats, in P388 lymphocytic leukemia in mice, and in S-180 sarcoma in mice.

Although DFMO can effectively block tumor putrescine biosynthesis, the resultant antitumor effect is cytostasis, not cytotoxicity. For example, DFMO reduces the growth rate of an MCA sarcoma, but does not produce tumor regression. This finding is consistent with reports of other investigators who showed that DFMO is a cytostatic agent. However, studies indicate that a significant role may exist for DFMO agents, permitting the future development of combination chemotherapeutic regimens which incorporate DFMO.

The initial promise of DFMO as a therapeutic ODC inhibitor for use in the treatment of various neoplasias has dimmed somewhat because, although DFMO does, in fact, irreversibly inhibit ODC activity, cells treated in vivo with DFMO significantly increase their uptake of exogenous putrescine as described in U.S. Pat. No. 4,925,835. The intercellular transport mechanisms of the cell do an "end run" around the DFMO-impaired ODC activity by importing putrescine from the extracellular milieu. Therefore, DFMO's effect in vivo is far poorer than in vitro. So, while DFMO treatment effectively inhibits intracellular putrescine neogenesis, it also results in increased uptake of extracellular putrescine, thereby offsetting its ODC inhibitory effect.

This problem is compounded by the fact that putrescine is present in many common foods, such as grapefruit juice, which contains approximately 400 ppm putrescine. This makes it virtually impossible to provide a patient a nutritionally sufficient diet which is free of putrescine. Therefore, DFMO-treated cells are capable of importing sufficient amounts of extracellular putrescine to support cell division.

Strategies to make DFMO more acceptable to human patients are described in U.S. Pat. No. 4,859,452 (incorporated by reference). Formulations of DFMO are described which include essential amino acids in combination with either arginine or ornithine to help reduce DFMO-induced toxicities.

C. O6-Alkyguanine-DNA Alkyltransferase Inhibitors

O6-alkylguanina-DNA alkyltransferase (AGT) is a target for inhibitory drugs such as temozolomide. Other AGT inhibitors may also prove useful in accordance with the disclosed methods.

D. Radiation

Factors that cause DNA damage and have been used extensively for cancer therapy and include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

E. Surgery

Approximately 60% of persons with cancer will undergo surgery of some type, which includes preventative, diagnostic or staging, curative and palliative surgery. Curative surgery as a cancer treatment may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

5. LIPOSACCHARIDE BINDING PROTEIN

A. LBP

Lipopolysaccharide binding protein is a protein that in humans is encoded by the LBP gene. LBP is a soluble acute-phase protein that binds to bacterial lipopolysaccharide (or LPS) to elicit immune responses by presenting the LPS to important cell surface pattern recognition receptors called CD14 and TLR4. The protein encoded by this gene is involved in the acute-phase immunologic response to gram-negative bacterial infections. Gram-negative bacteria contain a glycolipid, lipopolysaccharide (LPS), on their outer cell wall. Together with bactericidal permeability-increasing protein (BPI), the encoded protein binds LPS and interacts with the CD14 receptor, probably playing a role in regulating LPS-dependent monocyte responses. Studies in mice suggest that the encoded protein is necessary for the rapid acute-phase response to LPS but not for the clearance of LPS from circulation. This protein is part of a family of structurally and functionally related proteins, including BPI, plasma cholesteryl ester transfer protein (CETP), and phospholipid transfer protein (PLTP). This gene is found on chromosome 20, immediately downstream of the BPI gene. Lipopolysaccharide-binding protein has been shown to interact with CD14, TLR2, TLR4 and the co-receptor MD-2.

B. LBP Conjugates and Imaging

As first reported here by the inventors, LBP levels are elevated in high-grade human patient gliomas compared with tumors classified as low-grade gliomas. Thus, LBP conjugates for use in accordance with diagnostic methods disclosed herein include diagnostic conjugates of LBP linked to fluorescent labels, radioactive labels and contrast agents. These conjugates can be administered to a subject and their presence in the body, and in particular at glioma sites, can be determined using hand-held fluorescence scanners, near infrared scanners, MRI devices, and PET scanners. This approach can also be used to monitor efficacy of treatments, with reductions in LBP levels indicating therapeutic benefit.

6. PHARMACEUTICAL FORMULATIONS

The present invention discloses numerous compositions, which in certain aspects of the invention, are administered to animals. For example, 2,4-ds-PBN, as well as various secondary chemotherapeutic agents, will be formulated for administration. Where clinical applications are contemplated, it will be necessary to prepare pharmaceutical compositions of these compounds and compositions in a form appropriate for the intended application. Generally, this will entail preparing compositions that are essentially free of pyrogens, as well as other impurities that could be harmful to humans or animals.

One will generally desire to employ appropriate salts and buffers to render agents suitable for introduction into a patient. Aqueous compositions of the present invention comprise an effective amount of the agent, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients, such as other anti-cancer agents, can also be incorporated into the compositions.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

An effective amount of the agents is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

A. Enteral Administration

The active compounds of the present invention can advantageously be formulated for enteral administration, e.g., formulated for oral administration. The pharmaceutical forms may include sesame oil, peanut oil or aqueous propylene glycol; and sterile powders for the extemporaneous preparation of ingestible compositions, including tables, pills and capsules. Also, it is contemplated that the agents of the present invention can be provided in the form of a food additive and incorporated into a daily dietary program. All of these forms are generally selected to be sterile and stable under the conditions of manufacture and storage.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the particular methods of preparation are vacuum-drying and freeze-drying techniques which yield a powder of the active ingredient plus any additional desired ingredient from a previously sterile-filtered solution thereof.

B. Other Routes of Administration

In addition to the compounds formulated for enteral administration, parenteral formulations such as intravenous or intramuscular injection are envisioned. Administration may also be nasal, buccal, rectal, vaginal or topical. Alternatively, administration may be by intradermal, subcutaneous, or intraperitoneal injection. Also contemplated is continuous perfusion via catheter. Such compositions would normally be administered as pharmaceutically acceptable compositions, described supra.

7. EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute specifically contemplated modes for its practice. However, those of skill in the art should, in light of the present disclosure, appreciate that many changes can be made in the specific embodiments which are disclosed and still obtain a like or similar result without departing from the spirit and scope of the invention.

Example 1

Introduction and Study Design

Orthotopic G55 human GBM xenografts in nude mice is an established GBM model that the inventor has used in previous publications, and continues to use in his group. This model emulates a very aggressive GBM. For this model, the inventor had previous data for animal survival, tumor volume and vascular perfusion data for untreated animals, as well as TMZ-treated animals. He also had preliminary data that indicates that G55 cells are TMZ-resistant, and therefore this finding further supports the use of these cells as an ideal xenograft model for TMZ-resistance.

The inventor conducted a study with four treatment groups. For two groups, the inventor required a minimum of 5 animals per group. These were the OKN alone, and OKN+TMZ groups. For the other two groups (untreated and TMZ alone), the inventor included preexisting data to make up a group of 5 for each, and he included 2 untreated and 2 TMZ in the study conducted.

The inventor used MRI to obtain tumor volumes that were used to assess treatment response. He also obtained vascular perfusion data to assess the effects of treatment on tumor vascularity. Tumor vascular perfusion rates (measured as relative cerebral blood flow or rCBF) are calculated from the perfusion images. Tumor vascular perfusion rates are decreased in untreated tumors due to a disorganized vasculature due to angiogenesis. From normalized differences in rCBF, this would result in a substantial change in rcBF. Restoration of the tumor vascular perfusion rates via anti-cancer treatment can be indicative of an anti-angiogenesis effect. From normalized changes in rCBF, this would result in a relatively small difference in rCBF if the treatment effect had affected tumor vasculature. The inventor also assessed percent animal survival. For the MRI study, he initially indicated that a minimum of 3 time points was needed for the untreated group, and at least 5 time-points for the treated animals to assess tumor growth and vascular changes with MRI, whereas in actuality the inventor obtained at least 5 time-points for the untreated mice and well over 10 time-points for the treated mice, due to a positive treatment response.

The inventor also discovered a potential biomarker, LBP (lipopolysaccharide binding protein), that is elevated in tumors of rat F98 glioma-bearing rats (assessed by ELISA), and in GBM human tissue samples (assessed by immunohistochemistry). This biomarker was discovered from microarray data from the rat F98 glioma model where untreated tumors had high levels of LBP, and OKN-007 treatment had a >2-fold decrease in gene expression for LBP. Also in the rat F98 glioma model, OKN-007 was found to significantly decrease LBP protein levels (assessed by ELISA) in both tumor tissue ($p<0.0001$) and blood serum ($p<0.001$) when compared to untreated tumor-bearing animals. The inventor used an ELISA kit for LBP to assess this biomarker as an efficacy marker in both G55-tumor-bearing mice in both tumor tissue and blood serum, either untreated or treated with TMZ, OKN-007 or TMZ +OKN-007.

Example 2

Methods

Cell culture. G55 cells were obtained from Dr. Michael E. Sughrue (Univ. of Oklahoma Health Sciences Center). G55 cells were cultured in DMEM (LifeTechnologies, Waltham, Ma.) supplemented with 10% cosmic calf serum (CCS; HyClone, Logan, Utah) and 1% penicillin/streptomycin.

Mice and Treatments. Animal studies were conducted in accordance to the OMRF IACUC (Institutional Animal Care and Use Committee) policies, which follow NIH guidelines. Two-month-old male nude mice (Hsd:Athymic Nude-Foxnlnu mice; Harlan Inc., Indianapolis, Ind.) were implanted intra-cerebrally with human G55 xenograft cells ($1\times10^7$) per mL suspended in 4 µL in cell culture media of 1% aragose solution. Once tumors reached 10-15 mm$^3$ (determined via MRI), mice were either treated every 3 days with OKN-007 (150 mg/kg; via drinking water continuously) or TMZ (30 mg/kg via gavage every 3 days). TMZ was dissolved in 5% DMSO and 5% solutol-15 in sterile saline. Mice were treated until the tumor reached 100-150 mm$^3$ or for a total of up to 60 days after tumors were detected by MRI (>5 mm$^3$).

MRI. MRI experiments were performed on a Bruker Bio-spec 7.0 Tesla/30-cm horizontal-bore magnet imaging system. Animals were immobilized by using 1.5-2.5% isoflurane and 0.8 L/min $O_2$ and placed in a 72-mm quadrature volume coil for signal transmission, and a surface mouse-head coil was used for signal reception. T2-weighted imaging was obtained, and tumor volumes were calculated from MRI datasets.

Perfusion imaging. In order to assess microvascular alterations associated with tumor capillaries, the perfusion imaging method, arterial spin labeling (ASL), was used. Perfusion maps were obtained on a single axial slice of the brain located on the point of the rostro-caudal axis where the tumor has the largest cross-section. Five regions of interest (ROIs) were manually outlined around the tumor, and appropriate ROIs were also taken from the contralateral side of the brain for comparison purposes. To calculate the differences in rCBF values, tumor rCBF values were obtained at late (days 18-26 following intracerebral implantation of cells for untreated mice) and early (days 10-13 following cell implantation) tumor stages, and normalized to rCBF values in the contralateral brain region of corresponding animals.

Lipopolysaccharide binding protein (LBP) ELISA assay. The LBP ELISA kit (Antibodies-Online.com; ABIN370808) is specific for mouse LBP levels in serum, plasma and tissue samples. This is a colorimetric assay that was read on a micro plate reader for measurement of absorbance at 450/620 nm. LBP concentrations were calculated from a standard curve and multiplied by appropriate dilution factors.

Statistical analyses. Survival curves were analyzed using Kaplan-Meier curves. Tumor volumes, changes in normalized rCBF, and LBP levels were compared by two-way ANOVA with multiple comparisons. Data were represented as mean±SD, and P-values of either *0.05, 0.01, *0.001, and ****0.0001 were considered statistically significant.

Example 3

Results

Animal survival (see FIG. 1). The percent animal survival data indicated that 60% of the combined therapy (OKN-007+TMZ)-treated mice remained alive 60 days following tumor detection and treated for over 50 days. One of the OKN-007-treated mice (20% of the mice treated) was also alive 60 days following tumor detection. Statistical analysis indicated that all of the treated mice (either OKN-007 alone, TMZ alone or combined therapy) were found to have a significant increase in percent survival, when compared to untreated (UT) G55 glioma-bearing mice. It was also found that the combined therapy mice had a significantly longer survival than TMZ-treated mice. There was no significance between the OKN-007-treated and combined therapy mice. If the animal group numbers were larger, perhaps a significant difference could be obtained between the OKN-007-treated and combined therapy mice, as the p-value was 0.07 between these two groups.

Figure 2:
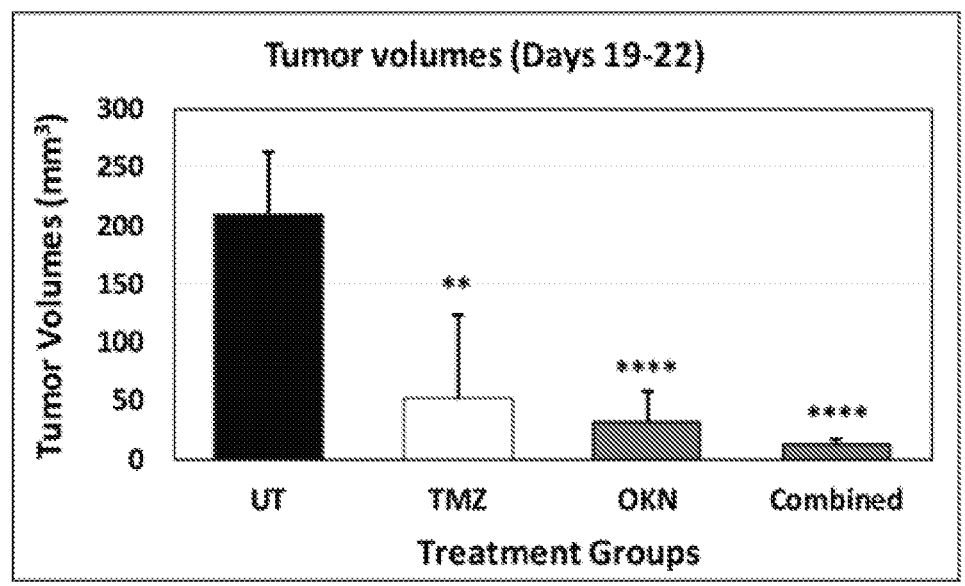
FIG. 2: In vivo tumor volumes ($mm^3$) obtained at days 19-22 following MRI detection of tumors (>5 $mm^3$).
Figure 3:
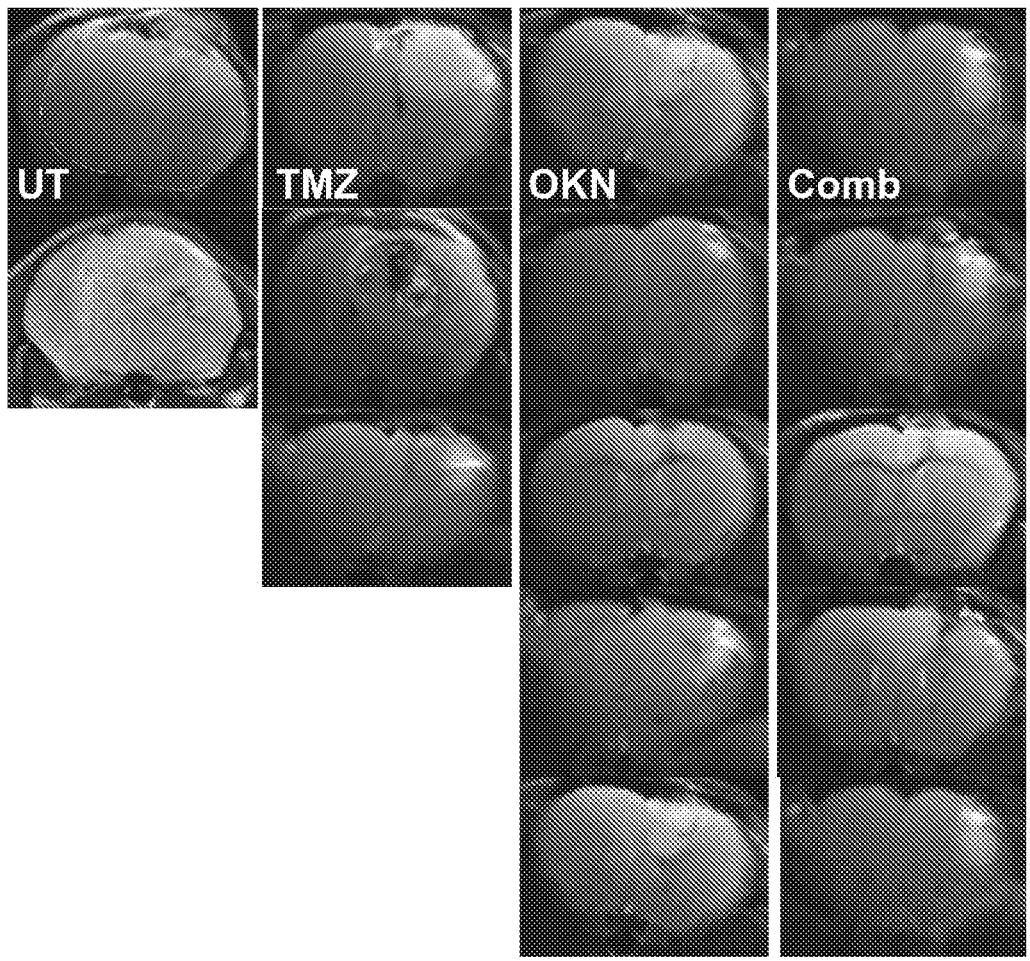
FIG. 3: MR images depicting tumors in the mid-tumor region (maximal tumor) for each treatment group (TMZ, OKN-007 (01(N), combined OKN-007 and TMZ (Comb), or untreated (UT).
Figure 4:
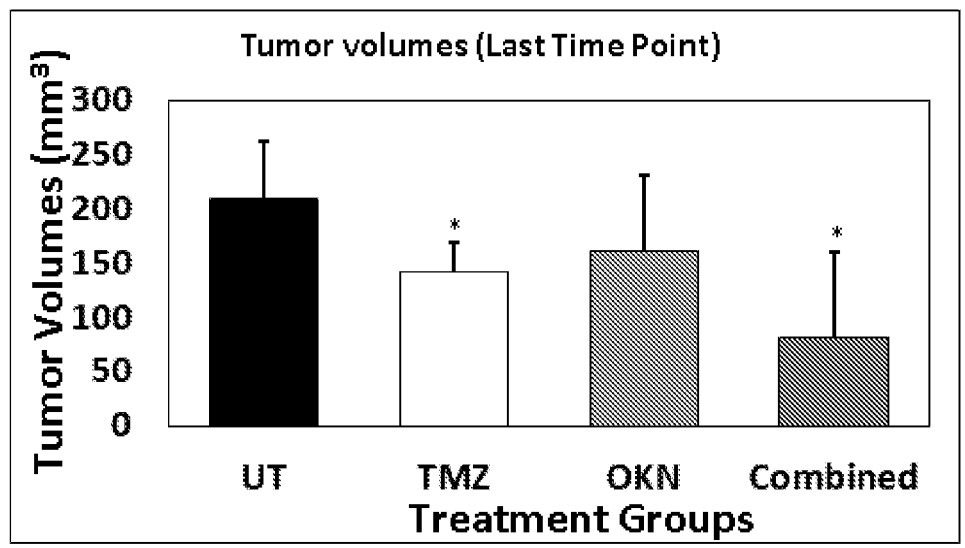
FIG. 4: Tumor volumes obtained at the last MRI time-point for each treatment group (UT, TMZ, OKN or combined treatments).
Figure 5A:
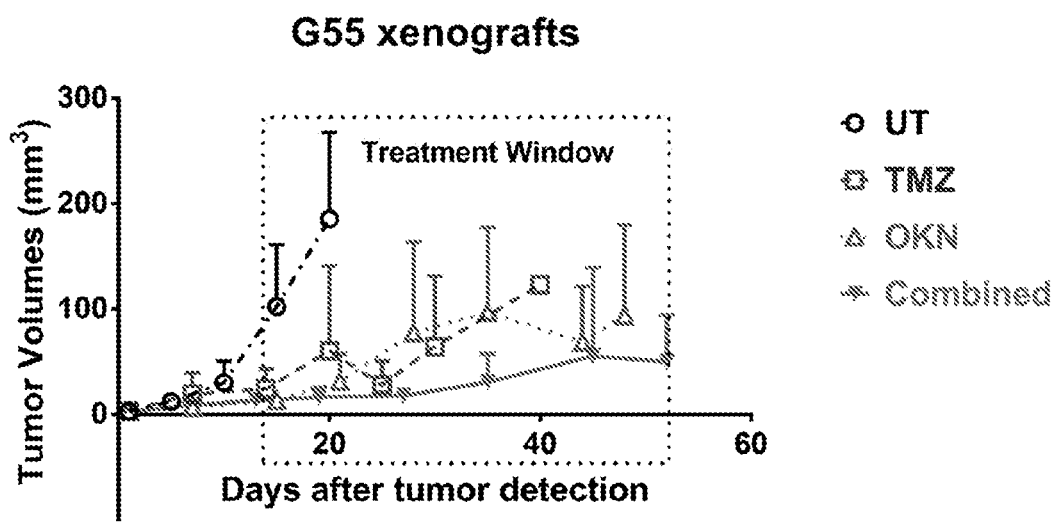
FIG. 5A: Tumor volumes (means±S.D.) obtained at multiple time-points for each treatment group (UT: black open circle with dash-dot line; TMZ: blue open square with a dash line; OKN: green open upward triangle with a dot line; Combined: red closed downward triangle with a solid line). The treatment window initiated when tumors were >10 $mm^3$ for up to >50 days.

Tumor volumes (see FIGS. 2-4). The tumor volumes were compared at the same time-period when the UT mice were euthanized, i.e., tumor volumes reached 150 mm$^3$ or larger (at 19-22 days following tumor detection), as well as at the last time-point for each treatment group. At 19-22 days following tumor detection, mice that were treated with either TMZ, OKN-007 or combined therapy, were all found to have significantly decreased tumor volumes when compared to UT mice (FIG. 2). None of the treated mice were found to significantly differ from each other in tumor volumes, however the combined therapy had the lowest tumor volume mean when compared to either TMZ- or OKN-007-treated mice. As the sample sizes were small (n=5), there may be a significant difference between treatment groups if the animal numbers were increased. The TMZ group had a large variance, which the inventor has also observed in two other studies that he have conducted. Representative MR images depicting tumors (mid-tumor regions) are also shown for each treatment group investigated (FIG. 3). At the last time-point for each treatment group, the tumor volumes for the TMZ and combined therapy groups were found to be significantly smaller when compared to UT mice (FIG. 4). Due to the large variance in the OKN-007-treated group, there was no significant difference in tumor volumes when compared to UT mice, or any of the other treated groups (TMZ alone, or combined therapy). Tumor volumes obtained at multiple time-points are depicted in the graph below (FIG. 5A). A treatment window is depicted, where tumors are treated when tumors reach≥10 mm$^3$.

Figure 5B:
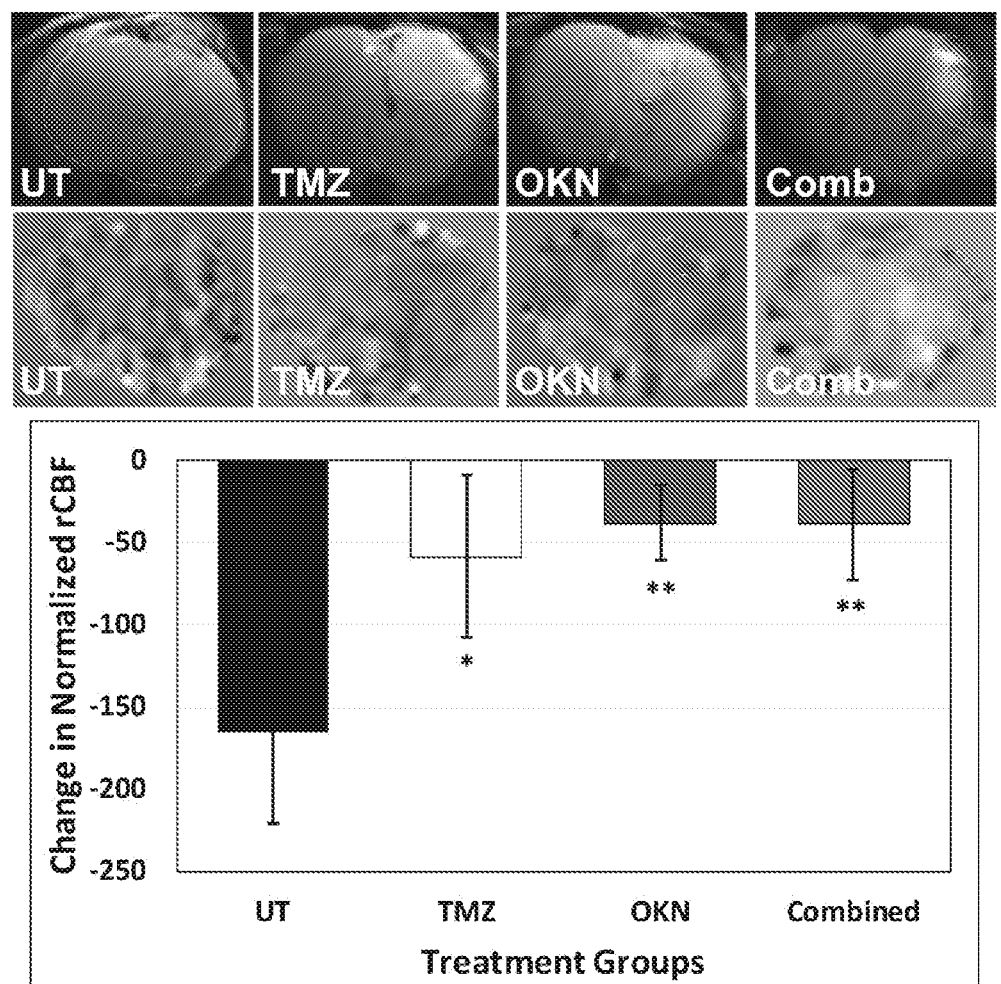
FIG. 5B: Changes (rCBF in tumors at 21-22 days following tumor detection minus rCBF at initial tumor detection) in normalized (normalized to contralateral or normal brain tissue) rCBF values in UT, TMZ, OKN or combined treated G55 glioma-bearing mice.

Tumor vasculature perfusion rates (normalized differences in rCBF) (see FIG. 5B). Normalized differences in tumor rCBF were found to significantly decrease in all treated mice, compared to UT mice. There were no significant differences between treated groups, due to the small number of animals per group, however both the combined therapy and OKN-007-treated groups seemed to have more normalized perfusion rates in their tumors, compared to TMZ treatment. Representative morphological MR images and their corresponding perfusion maps are shown for each treatment group.

Figure 6:
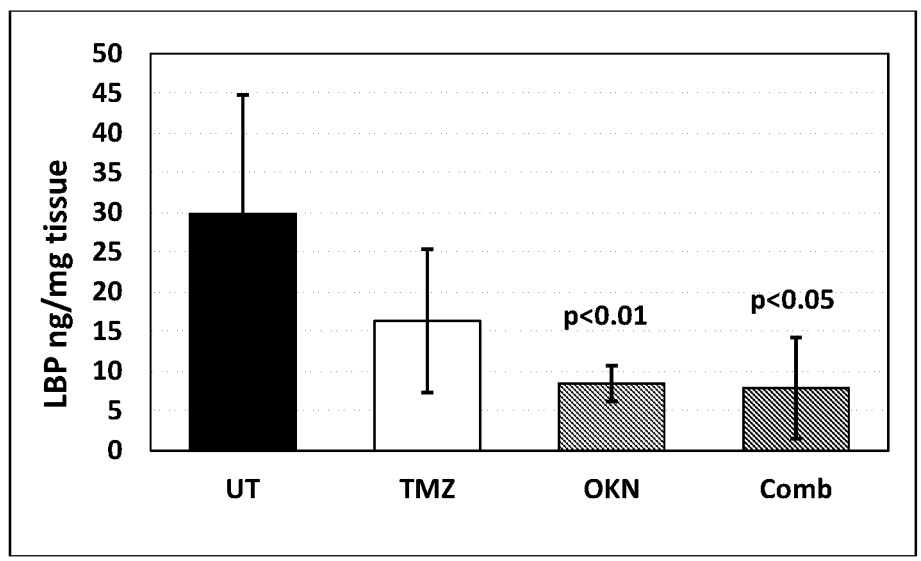
FIG. 6: Ex vivo LBP levels measured from ELISA in tumor tissue lysates obtained from UT, TMZ, OKN or combined treated G55 glioma-bearing mice.
Figure 7:
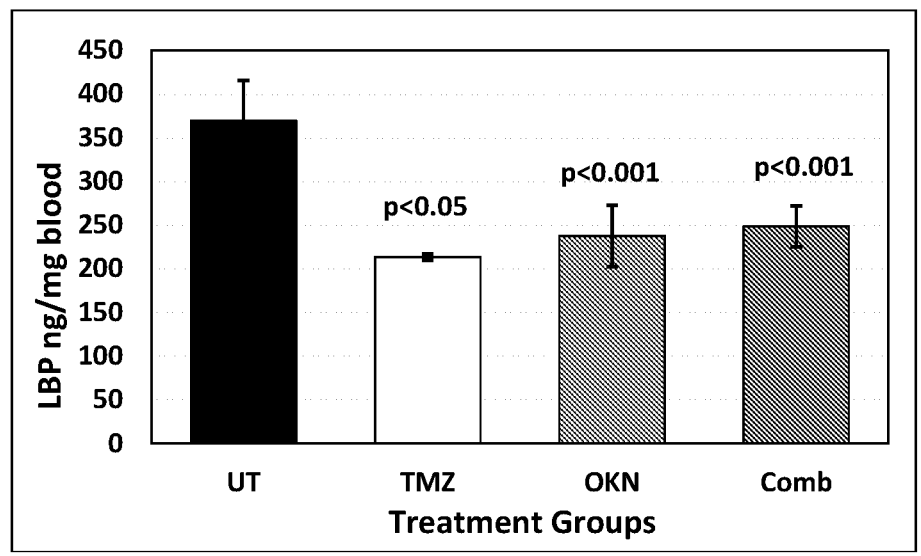
FIG. 7: Ex vivo LBP levels measured from ELISA in blood sera obtained from UT, TMZ, OKN or combined treated G55 glioma-bearing mice.

LBP ELISA assay (see FIGS. 6 and 7). The LBP levels in the OKN-007-treated or combined therapy mice were significantly less in tumor tissues, compared to UT mice (FIG. 6). In tumor tissues, the TMZ-treated group LBP levels were not found to be significantly different to UT mouse tumors. There was no significant difference between the OKN-007-treated group from the combined therapy in tumor LBP levels. The effect could have been mainly contributed by the effect of OKN-007. The serum LBP levels were found to be significantly less in all treatment groups compared to UT mouse samples, indicating a general treatment response (FIG. 7).

In vitro $IC_{50}$ assessment of TMZ-resistant and TMZ-sensitive GBM cell lines combined with OKN-007 (FIG. 8). OKN-007 has been previously shown by the inventors that it has anti-tumor activity in glioblastoma (GBM) pre-clinical models. In vitro data demonstrate that OKN-007 can decrease TMZ (temozolomide)-resistant GBM cell lines (T98G and G55), when they are combined together.

Liposaccharide binding protein (LBP). During a detailed study assessing the mechanism of OKN-007 action, a transcriptional microarray was used to elucidate specific genetic alterations associated with OKN-007 treatment in a rat F98 glioma model. LBP was down-regulated in OKN-treated rat F98 gliomas (compared to untreated), and is associated with TGF-β1. LPB (lipopolysaccharide-binding protein), which was discovered 27 years ago and named after the ability to bind LPS, is needed to combat infections, and is involved in innate and adaptive immunity. The main mechanism of action of LBP is still not clear.

Figure 9:
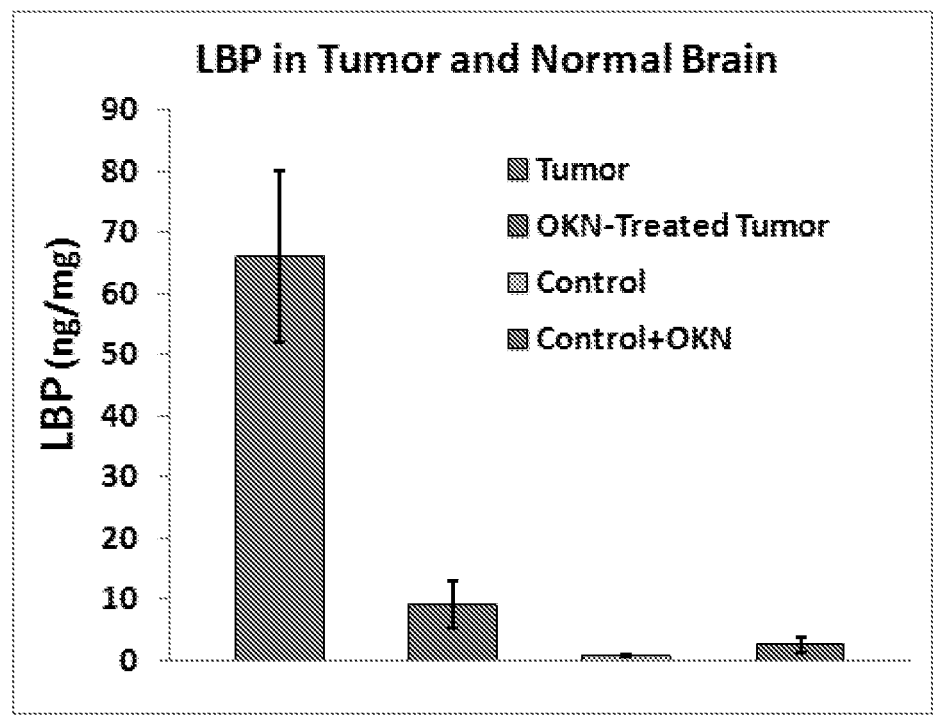
FIG. 9: OKN-007 effect on LBP in glioma-bearing rat tumors. ELISA assessment of LBP performed on tissue lysates from F98 glioma-bearing animals showed expression differences during the therapy with OKN-007. Levels of LBP in the tumor bearing animals were significantly elevated compared to the non-tumor control group, and OKN-007 treatment brought the levels of LBP close to the non-tumor controls.
Figure 10:
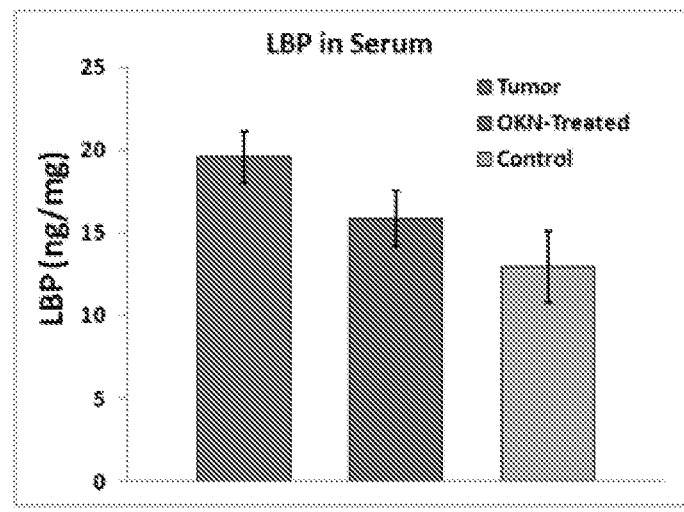
FIG. 10: OKN-007 effect in LBP in glioma-bearing rat sera. ELISA assessment of LPB using the blood serum from the same animals from FIG. 9 confirmed that LPB can serve as a serum biomarker that can predict the therapy outcome of OKN-007 in gliomas.

OKN-007 effects on LPB (FIGS. 9 and 10). Levels of protein LBP in tumor tissues of untreated (Tumor) and OKN-007-treated (OKN-Treated Tumor) F98 glioma bearing rats are shown in FIG. 9. Normal brain tissues were obtained from untreated (Control) and OKN-007-treated (Control+OKN) rats. There was a significant decrease in LBP levels in OKN-007-treated gliomas compared to untreated ($p<0.0001$). Control tissues (untreated or treated) were also significantly lower ($p<0.0001$)

Levels of protein LBP in serum of untreated (Tumor) and OKN-007- treated (OKN-Treated) F98 glioma rats are shown in FIG. 10. Serum from normal rats (Control) was also obtained. Serum levels of LBP were significantly lower in OKN-treated F98 glioma-bearing rats compared to untreated tumor-bearing rats ($p<0.001$), in normal rats vs. untreated tumor-bearing ($p<0.0001$), or normal rats vs. OKN-007-treated glioma-bearing rats ($p<0.05$).

Figure 12:
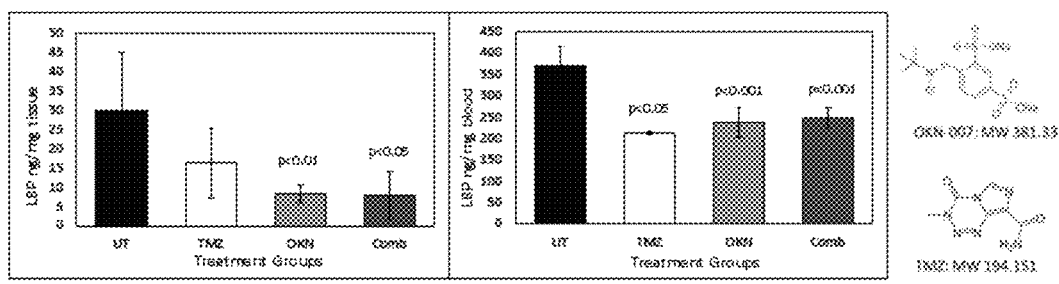
FIG. 12: LBP as a marker for OKN efficacy. For each treatment group, LBP levels were assessed by ELISA from blood and tumor tissue samples at the end of the study. All treatments were found to significantly decrease LBP in blood compared to UT mice with G55 gliomas. OKN and combined treatments were found to significantly decrease LBP in tumor tissue compared to UT mice with G55 gliomas. In tumor tissues or blood, there seemed to be no difference between OKN or combined therapies on LBP levels.

Immunohistochemistry levels of LBP in a high grade glioma (FIG. 11A), compared to low grade glioma (FIG. 11B), indicate a significant increase in LBP in high grade gliomas (FIG. 11C). LBP was found to be significantly lowered by OKN-007 or by combined OKN-007+TMZ treatment in G55 human GBMV xenografts in nude mice in both tumor tissues (left graph) and blood serum (right graph), compared to untreated tumors. FIG. 12.

Conclusions. The combined therapy (OKN-007+TMZ) seemed to have an overall favorable response in increased animal survival, decreased tumor volumes, decreased change in rCBF, and decreased levels of LBP in both tumor tissue and blood serum. It is possible that an increase in animal numbers would show significant differences in animal survival, tumor volumes and changes in rCBF when comparing the 3 treatment groups (TMZ alone, OKN-007 alone and combined therapy). It would also be advantageous to conduct the study in another TMZ-resistant model (either xenograft model of another TMZ-resistant GBM cell line, or a patient-derived xenograft model using GBM cells from a patient that failed TMZ treatment). In conclusion, the data supports that combined OKN-007 and TMZ treatment indicates an overall improvement compared to either TMZ or OKN-007 sole treatments and should be considered for clinical investigation. However, in order to convince other cancer researchers regarding a publication, an increase in animal numbers, and perhaps using another xenograft model, would strengthen the overall outcome.

Example 4

Materials and Methods

In Vivo Studies

Mice and Treatments. Animal studies were conducted in accordance to the OMRF IACUC (Institutional Animal Care and Use Committee) policies, which follow NIH guidelines. For the F98 rat glioma cell implantation model, F98 cells ($10^5$ in 10-μl volume) were intracerebrally implanted with a stereotaxic device (2 mm lateral and 2 mm anterior to the bregma, and at a 3 mm depth) in a total of 15 Fischer 344 rats (male 200-250 gm). The animals were divided into two groups once tumors reached 10-20 mm$^3$ in volume (as determined by MRI): OKN-007 treated (n=8) and untreated (UT) (n=7) groups. Rats were treated until tumors reached 200-250 mm$^3$ in volume or for a total of 4-6 weeks. For the G55 GBM cell implantation model, two-month-old male nude mice (Hsd:Athymic Nude-Foxnlnu mice; Harlan Inc., Indianapolis, IN) were implanted intracerebrally with human G55 xenograft cells ($1\times10^6$) per mL suspended in 4 μL in cell culture media of 1% agarose solution. Once tumors reached 10-15 mm$^3$ (determined via MRI), mice were either treated daily with OKN-007 in the drinking water (150 mg/kg; 0.20% w/v for a 20 g mouse), or every 3 days with TMZ (30 mg/kg). OKN-007 was dissolved in water and made fresh every 2 days. Water bottles were weighed, and the amount of OKN-007 consumed per mouse was determined. No significant deviation was observed in the volume of liquid uptake of OKN-007 in these mice. The average intake of OKN-007 was approximately 140-150 mg/kg/day/mouse. TMZ was dissolved in 5% DMSO and 5% solutol-15 in sterile saline and administered via gavage. Mice were treated until the tumors reached 100-150 mm$^3$ or for a total of 4-6 weeks. All groups were stratified to ensure that tumor sizes were similar before initiation of treatment.

Magnetic resonance imaging (MRI). MRI experiments were performed on a Bruker Bio-spec 7.0 Tesla/30-cm horizontal-bore magnet imaging system. Animals were immobilized by using 1.5-2.5% isoflurane and 0.8 L/min $O_2$ and placed in a 72-mm quadrature volume coil for signal transmission, and either a surface rat-head or mouse-head coil were used for signal reception. T2-weighted morphological imaging was obtained with a slice thickness of 0.5 mm, a FOV of 4×5 cm$^2$ for rats or 2×2 cm$^2$ for mice, with an approximate in-plane resolution of 150 μm for rats and 80 μm for mice, with a repetition time (TR) of 3000 ms and an echo time (TE) of 63 ms, for a total acquisition time of 13 min. Tumor volumes were calculated from 3D MRI slices rendered MRI datasets, using Amira v5.6.0 (FEI) (Zhao et al., 2018; Tang et al., 2011; Tang et al., 2016).

Perfusion imaging. In order to assess microvascular alterations associated with tumor capillaries, the perfusion imaging method, arterial spin labeling (ASL), was used as previously described (Ziegler et al., 2017). Perfusion maps were obtained on a single axial slice of the brain located on the point of the rostro-caudal axis where the tumor had the largest cross-section. Five regions of interest (ROIs) were manually outlined around the tumor, and appropriate ROIs were also taken from the contralateral side of the brain for comparison purposes. To calculate the differences in rCBF values, tumor rCBF values were obtained at late (days 18-26 following intracerebral implantation of cells for untreated mice) and early (days 10-13 following cell implantation) tumor stages and normalized to rCBF values in the contralateral brain region of corresponding animals. Tumor volumes were transposed from morphological image data sets.

RNA isolation and preparation. For the rat F98 glioma study, all rats were euthanized after the last MRI examination. The brain of each animal was removed, and snap frozen in liquid nitrogen, before storage in a −80° C. freezer. Total RNA from all tumor tissues from all treatment groups was purified with an RNeasy Mini Kit (Qiagen), and quantified by spectrophotometry (Nanodrop). cDNA was synthesized using SuperScript IV Reverse Transcriptase Kit (Invitrogen).

Microarray analysis. The Illumina TotalPrepTM RNA Amplification Kit was used for labeling cRNA (Ambion, Austin, Tex.), as previously described (Griffins et al., 2009). Four×four treated/untreated samples were profiled using Affymetrix RaGene-1_0-st-v1 microarrays. Exon-level-summarized measures were quantile-normalized and tested for differential expression using Significance Analysis of Microarrays (SAM, [PMID: 11309499]) at a false discovery rate (FDR) <40% and fold change <1.5. Functional enrichment analysis was performed using Ingenuity Pathways Analysis (IPA) (Ingenuity® Systems, world-wide-web at ingenuity.com).

Histology and immunohistochemistry (IHC). All mice were euthanized after the last MRI examination. Perfusion fixation (10% neutral buffered formalin administered via a tail-vein injection) was used on anesthetized (Isoflurane) mice, and whole brain of each animal was removed, further preserved in 10% neutral buffered formalin, and processed routinely. Paraffin-embedded tissues were sectioned in 5 µm sections, mounted on super frost plus® glass slides, stained with hematoxylin and eosin (H&E), and examined by light microscopy. Immunohistochemistry (IHC) was done to establish TGFβ1 levels by staining tissue samples with anti-TGFβ1 antibody (rabbit anti-TGFβ1, cat. No. 250876, 1 mg/mL, ABBIOTEC, San Diego, Calif.). For TGFβ1 IHC, sections were incubated in an antigen retrieval solution (citrate buffer, pH 6, Vector Laboratories, Burlingame Calif.) for 20 min in a rice steamer, followed by a 20 min cool down in deionized water.

Statistical Analysis. Survival curves were analyzed using Kaplan-Meier curves. Tumor volumes, changes in normalized rCBF, and tumor blood volumes were analyzed and compared by two-way ANOVA with multiple comparisons. Data were represented as mean±SD, and P-values of either *0.05, 0.01, *0.001, and ****0.0001 were considered statistically significant. For microarray data, random variance t-statistics for each gene was used (Wright and Simon, 2003).

In Vitro Studies

Cells and culture media. Most GBM cells were obtained from the American Tissue Culture Collection (ATCC; Manassas, VA, USA) (U-138—ATCC (CRL-HTB-16) glioblastoma; LN-18— ATCC (CRL-2610) glioblastoma; LN-229—ATCC (CRL-2611) glioblastoma; and T-98G—ATCC—(CRL-1690). U-251 GBM cells were obtained from Sigma-Aldrich (N#09063001 also known before as U-373 MG (ATCC® HTB-17)). G55 cells were obtained from Dr. Michael Sughrue, who was a resident at Univ. of California San Francisco (originally obtained from C. David James (Department of Neurological Surgery, UCSF, CA, USA), who characterized the cells).

Cells were cultured in Dulbecco's modified Eagle's medium (DMEM, Gibco BRL, Crand Island, N.Y., USA) supplemented with 10% fetal bovine serum (Gibco) in a standard humidified incubator at 37° C. under 5% $CO_2$.

$IC_{50}$ concentrations—Protocol for TMZ sensitivity determination. The sensitivities of the six glioma cell lines to TMZ were evaluated from the concentrations required for 50% growth inhibition ($IC_{50}$; also known as $GI_{50}$) in comparison with untreated controls (Wang et al., 2017). Briefly, cells were plated at $1 \times 10^4$ cells per well in 24-well, flat-bottomed plates and incubated with medium for 24 hrs. The cells were subsequently washed twice with medium and incubated further with fresh medium (control) or medium containing 0.1-1,000 µM of TMZ. Per each plate contained growth medium with +/−TMZ there was a plate with medium containing 1 mM OKN. After exposure to the various concentrations of TMZ for 72 hrs, cells were detached by trypsinization and the numbers counted. The experiments were repeated at least 4 times at each concentration.

RNA preparation. To avoid contributions from artificial sources in the experimentally measured expression patterns, each cell line was grown in four independent cultures, and the entire process was carried out independently on mRNA extracted from each culture.

Cell lines LN-18 and LN-229 were subjected to an assessment of their gene expression profile for 4 groups: cells, cells with TMZ, cells with TMZ-OKN combined treatment, cells with OKN. The extracted total RNA was purified with an RNeasy Mini Kit (Qiagen), quantified by spectrophotometry (Nanodrop).

Quantification of mRNA by real-time quantitative RT-PCR for HIF-1a, MPG and MGMT. Total RNA from all cell lines with all treatments was purified with an RNeasy Mini Kit (Qiagen), and quantified by spectrophotometry (Nanodrop). cDNA was synthesized using SuperScript IV Reverse Transcriptase Kit (Invitrogen).

Target gene mRNA was amplified and measured by Bio-Rad CFX96™ Real Time System. Gene expression was determined using the SYBR Select Master Mix (Applied Biosystems). Fluorescence signals, which are proportional to the concentration of the PCR product, are measured at the end of each cycle and immediately displayed on a computer screen, permitting real-time monitoring of the PCR. The reaction is characterized by the point during cycling when amplification of PCR products is first detected, rather than the amount of PCR product accumulated after a fixed number of cycles. The higher the starting quantity of the template, the earlier a significant increase in fluorescence is observed. The threshold cycle is defined as the fractional cycle number at which fluorescence passes a fixed threshold above the baseline. Fluorescence data were converted into cycle threshold measurements exported to Microsoft Excel. Glyceraldehyde-3-phosphatase dehydrogenase (GAPDH) mRNA expression levels were used as the quantitative internal control. For precise quantification, the mRNA expression level of each sample was normalized using the expression of the GAPDH gene.

All primers were synthesized by Integrated DNA Technologies. The primers used were:

```
HIF-1α:
                                          (SEQ ID NO: 1)
F 5'-GTCGGACAGCCTCACCAAACAGAGC-3'

(SEQ ID NO: 2)
R 5'-GTTAACTTGATCCAAAGCTCTGAG-3'.

For MGMT:
                                          (SEQ ID NO: 3)
F 5'-GGGTCTGCACGAAATAAAGC-3', (SEQ ID NO: 4)
R 5'-CTCCGGACCTCCGAGAAC-3' [6], (SEQ ID NO: 5)
5'-GTC CTA GTC CGG CGA CTT CC-3',
and (SEQ ID NO: 6)
5'-CTT GTC TGG GCA GGC CCT TTG C-3'
``` were used to amplify 603-bp transcripts of MPG [9].

ELISA for HIF-1a, MPG and MGMT. Protein expressions were assessed in all six glioma cell lines for all four groups of treatment (cell alone, cells with TMZ, cells with OKN, cells with combined OKN and TMZ). Cells were lysed before assaying. In brief, cells were washed by cold PBS gently, and then detached with trypsin, and collected by centrifugation at 1,000×g for 5 minutes. Then, cells were washed three times in cold PBS, then suspended in fresh lysis buffer. Lysates were centrifuged at 1,500×g for 10 minutes at 2-8° C. to remove cellular debris.

The assay is based on the sandwich ELISA principle. Each well of the supplied microtiter plate has been pre-coated with a target specific capture antibody. Standards or samples are added to the wells and the target antigen binds to the capture antibody. Unbound Standard or sample is washed away. A biotin-conjugated detection antibody is then added which binds to the captured antigen. Unbound detection antibody is washed away. An Avidin-Horseradish Peroxidase (HRP) conjugate is then added which binds to the biotin. Unbound Avidin-HRP conjugate is washed away. A TMB substrate is then added which reacts with the HRP enzyme resulting in color development. A sulfuric acid stop solution is added to terminate color development reaction and then the optical density (OD) of the well is measured at a wavelength of 450 nm±2 nm. The OD of an unknown sample can then be compared to an OD standard curve generated using known antigen concentrations in order to determine its antigen concentration.

The antigen concentration determined from ELISA was then normalized to the total protein concentration of each cell lysate in order to have comparison between groups. ELISA Kits for N-Methylpurine DNA Glycosylase (MPG) and for Hypoxia Inducible Factor 1 Alpha (HIF1a) were purchased from CLOUD-CLONE CORP.(CCC) and for Human MGMT from LifeSpan Biosciences, Inc.

RNA-seq. Prior to RNA-seq analysis quality control measures were implemented. Concentration of RNA was ascertained via fluorometric analysis on a Thermo Fisher Qubit fluorometer. Overall quality of RNA was verified using an Agilent Tapestation instrument. Following initial QC steps sequencing libraries were generated using the Lexogen Quantseq FWD library prep kit according to the manufacturers protocol. Briefly, the first strand of cDNA was generated using 5'-tagged poly-T oligomer primers. Following RNase digestion, the second strand of cDNA was generated using 5'-tagged random primers. A subsequent PCR step with additional primers added the complete adapter sequence to the initial 5' tags, added unique indices for demultiplexing of samples, and amplified the library. Final libraries for each sample were assayed on the Agilent Tapestation for appropriate size and quantity. These libraries were then pooled in equimolar amounts as ascertained via fluorometric analyses. Final pools were absolutely quantified using qPCR on a Roche LightCycler 480 instrument with Kapa Biosystems Illumina Library Quantification reagents. Sequencing was performed on an Illumina Nextseq 500 instrument with High Output chemistry and 75 bp single-ended reads.

Raw sequencing files were processed with bbduk (decontamination using Kmers) (Bushnell, 2014) trimming of poly A tails and adaptor sequences. Fastqc (Andrews, 2010) and multiQC (Ewels et al., 2016) were used to check the quality of the resulting fastq files. High-quality scores (phred scores) of 33-36 were present in all samples with 9.3+/−1.3 million reads each. Sorted bam files aligned with Tophat2 (Trapnell et al., 2009) to the GRCh38 genome were then provided to two separate pipelines in parallel, in order to analyze the robust responses from each package. Counts and differential gene expression were obtained with R using the 'GenomicAlignments' function 'summarizeOverlaps' and the negative binomial generalized linear modeling package DESeq2 (Love et al., 2014).

Cell migration. For the migration study, 6-well chambers with PDMS (polydimethylsiloxane) micro-channels inside were coated with 10 μg/ml of laminin (Sigma-Aldrich) in each well. G55 cells were seeded (50×10$^3$) in 100 μl and supplemented with 2 ml of media in each well. The chambers were incubated in the incubator at 37° C. with 5% $CO_2$ until scheduled time points. Some chambers were treated with OKN-007, TMZ or OKN-007 combined with TMZ (1 μL/mL media for both OKN-007 and TMZ, as well as when the two are combined), and for each treatment group one well was left untreated as a control. Images of the cells inside the microchannels were taken using an Olympus CK40 inverted microscope (Japan) under 10× and the distances of the same cells traveled were measured at 22 h, 28 h, and 46 h post seeding, cell migration speed (μm/h) was calculated. Each treatment was repeated at least 3 times and data shown as mean ±S.D.

Statistical Analysis. RT-PCR gene and ELISA protein levels, and cell migrations were analyzed and compared by two-way ANOVA with multiple comparisons. RNA-seq data were analyzed using FDR<0.05 from the Benjamini-Hochberg FDR values provided by DESeq2 (Love et al., 2014; Benjamini and Hochberg, 1995; Robinson et al., 2010). Data were represented as mean±SD, and P-values of either *0.05, 0.01, *0.001, and ****0.0001 were considered statistically significant.

Example 5

Results

Figure 13:
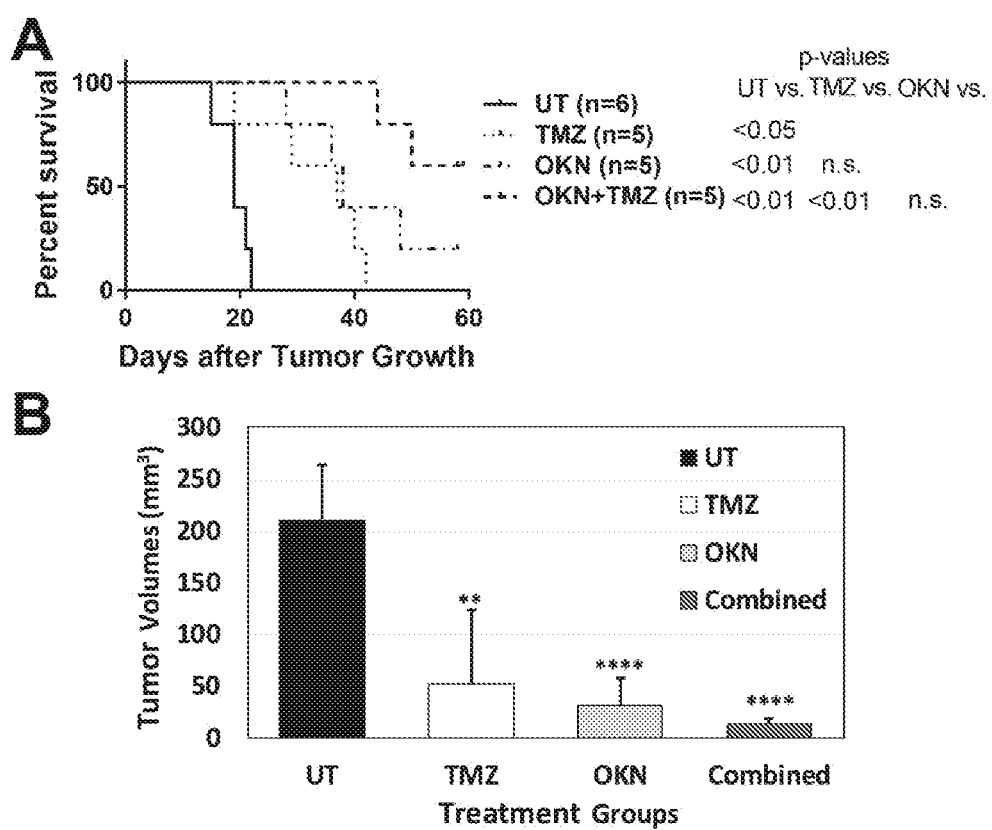
FIGS. 13A-B.

In vivo G55 orthotopic xenograft GBM model. The percent animal survival data indicated that 60% of the combined therapy (OKN-007+TMZ)-treated mice remained alive 60 days following tumor detection and treated for over 50 days (FIG. 13A). One of the OKN-007-treated mice (20% of the mice treated) was also alive 60 days following tumor detection. Statistical analysis indicated that all of the treated mice (either OKN-007 alone, TMZ alone or combined therapy) were found to have a significant decrease in percent survival, when compared to untreated (UT) G55 glioma-bearing mice. It was also found that the combined therapy mice had a significantly longer survival than TMZ-treated mice. There was no significance between the OKN-007-treated and combined therapy mice.

Figure 14:
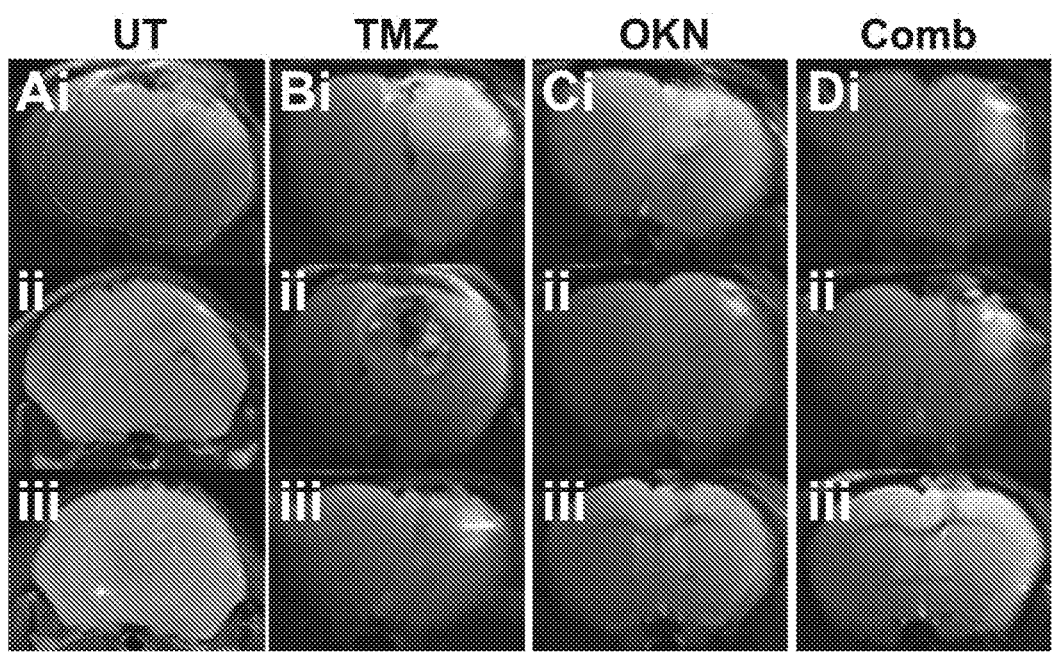
FIGS. 14Ai-Diii: Representative MR images depicting tumors in the mid-tumor region (maximal tumor) for (FIG. 14A) untreated (UT), or each treatment group (FIG. 14B) TMZ, (FIG. 14C) OKN-007 (OKN), or (FIG. 14D) combined OKN-007 and TMZ (Comb), at 19-22 days following tumor detection. For images labeled "i", the tumors are highlighted with a faint line to depict tumor boundaries. Images in panels "ii" or "iii" are other examples in treatment groups A-D, depicting either consistency in the UT group, or variability in the treatment groups. There were no detectable tumors in FIG. 14Ciii or FIG. 14Diii for the OKN-007- or combined-therapy groups, following treatment at this time-point range.

The tumor volumes were compared at the same time-period when the UT mice were euthanized, i.e., tumor volumes reached 150 mm³ or larger (at 19-22 days following tumor detection), as well as at the last time-point for each treatment group. At 19-22 days following tumor detection, mice that were treated with either TMZ, OKN-007 or combined therapy, were all found to have significantly decreased tumor volumes when compared to UT mice (FIG. 13B). None of the treated mice were found to significantly differ from each other in tumor volumes, however the combined therapy had the lowest tumor volume mean when compared to either TMZ- or OKN-007-treated mice. Representative MR images depicting tumors (mid-tumor regions) are also shown for each treatment group investigated (FIG. 14).

Figure 15:
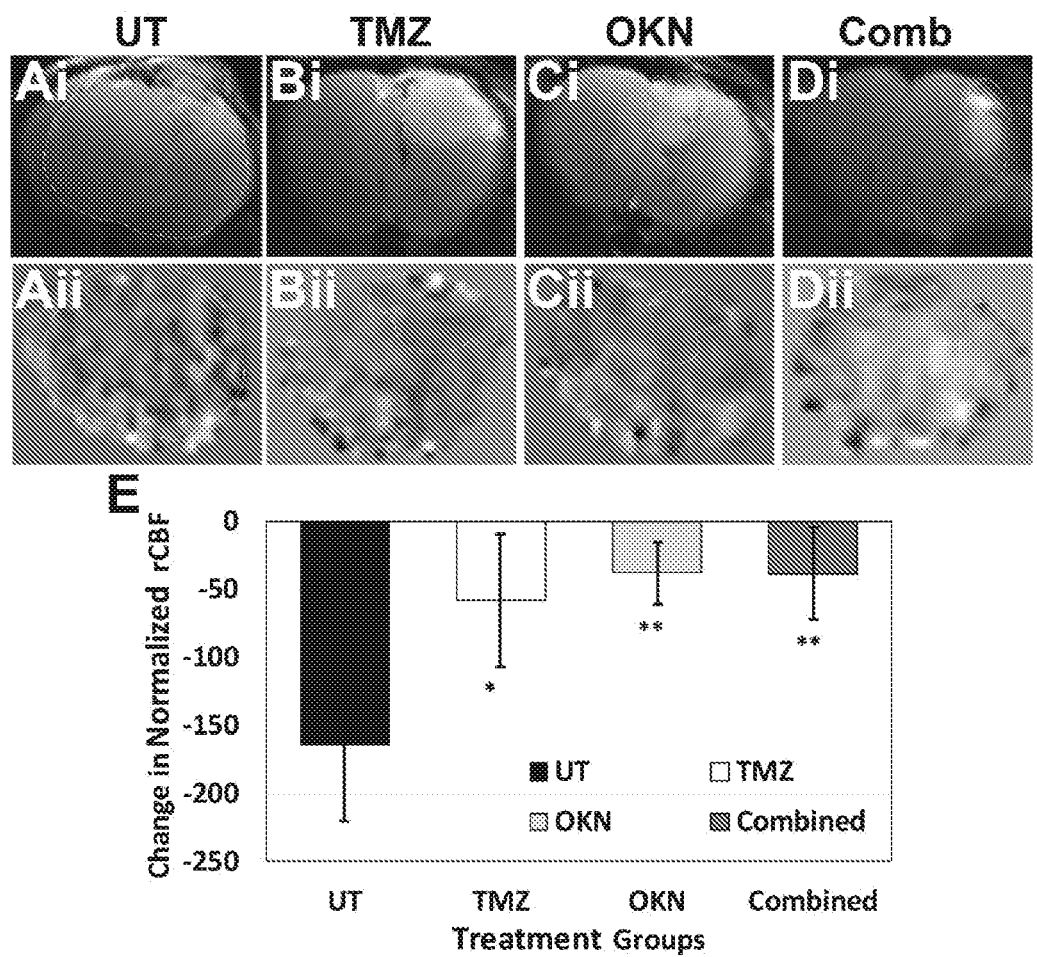
FIGS. 15Ai-E: Vascular changes as depicted by perfusion MRI [rCBF (relative cerebral blood flow) in tumors at 21-22 days following tumor detection minus rCBF at initial tumor detection] in normalized (normalized to contralateral or normal brain tissue) rCBF values for (FIG. 15A) UT, (FIG. 15B) TMZ, (FIG. 15C) OKN or (FIG. 15D) combined treated G55 glioma-bearing mice. The top panel of images labeled "i" are representative T2-weighted morphological MR images for each treatment group, whereas the images labeled "ii" are representative perfusion maps for each treatment group.
(FIG. 15E) Quantitative assessment of a change in normalized rCBF in UT and TMZ-, OKN-, or combined therapy-treated G55 glioma-bearing mice. All treatment groups had a significantly lower ($p<0.05$ or more) change in normalized rCBF, compared to the UT group.

Normalized differences in tumor rCBF were found to significantly decrease in all treated mice, compared to UT mice (FIG. 15E). There were no significant differences between treated groups, due to the small number of animals per group, however both the combined therapy and OKN-007-treated groups seemed to have more normalized perfusion rates in their tumors, compared to TMZ treatment. Representative morphological MR images (FIGS. 15-Di) and their corresponding perfusion maps (FIGS. 15A-Dii) are shown for each treatment group.

In vitro GBM cell study, From the in vitro GBM cell growth curves, it was established from the TMZ-sensitive cells (U251, LN229) that most of the cells were killed more than 50% with TMZ concentrations of 100 µM or less (Table 4). For the TMZ-resistant GBM cells (T98, LN18, U138, G55), the effect of combined therapy was substantial at TMZ concentrations less than 100 µM. The efficacy of combined therapy was significant.

TABLE 4-continued $IC_{50}$ values for human GBM cells treated with either TMZ alone (0, 0.1, 1, 10, 100 or 1000 µM) or TMZ combined with OKN (1 mM).

| Cell line | TMZ, µM | TMZ, µM + OKN-007 |
|---|---|---|
| LN18 | 773.7 | 31.9 |
| T98 | 438.3 | 295.4 |
|  | 447.2 | 138.9 |

A concentration of 1 mM OKN was found to be just as effective in reducing cell viabilities, compared to the 2 mM concentration for some cells (LN229, U138, G55). In the other cells (U251, T98, LN18) 2 mM OKN was found to be slightly more effective in reducing cell viabilities, compared to the 1 mM concentration.

HIF-1α, MGMT and MPG. RT-PCR (Table 5) indicated that HIF-1α gene-fold changes had increased in all TMZ-treated and OKN-007 +TMZ-treated cells. OKN-007 increased HIF-1α gene-fold changes in all cells, except T98 cells, which had decreased gene-fold changes. MGMT gene-fold change is decreased in LN18 cells treated with either TMZ or OKN-007. OKN-007 decreased MGMT gene-fold change in T98 cells. MGMT gene-fold changes are increased in U251 cells following either TMZ, OKN-007 or combined treatment. MGMT gene-fold changes are increased slightly in LN18 combined treatment. MPG gene-fold changes are increased in most cells following TMZ treatment, in OKN-007-treated G55 and U138 cells, and for G55, LN18 and U138 cells treated with OKN-007 combined with TMZ. There were decreases in MPG gene-fold changes with OKN-007-treatment for LN18, T98, U251 and LN229 cells, and also for T98 and LN229 cells treated with OKN-007 +TMZ.

TABLE 5

RT-PCR gene-fold changes for HIF-1α, MGMT and MPG in TMZ-resistant and TMZ-sensitive human GBM cells treated with either TMZ, OKN or combined OKN + TMZ, or untreated (UT).

| Cells | HIF-1α | | | | MGMT | | | | MPG | | | |
|---|---|---|---|---|---|---|---|---|---|---|---|---|
|  | UT | TMZ | OKN | Comb | UT | TMZ | OKN | Comb | UT | TMZ | OKN | Comb |
| TMZ-Resistant | | | | | | | | | | | | |
| G55 | 1.00 | 1.85 | 1.20 | 2.10 | — | — | — | — | 1.06 | 2.53 | 4.52 | 3.58 |
| LN18 | 1.03 | 2.11 | 1.35 | 2.76 | 1.06 | 0.77 | 0.42 | 1.26 | 1.00 | 2.95 | 0.60 | 5.40 |
| U138 | 1.00 | 2.05 | 2.93 | 3.17 | — | — | — | — | 1.13 | 7.14 | 11.10 | 12.70 |
| T98 | 1.00 | 1.72 | 0.58 | 1.56 | 1.00 | 1.07 | 0.54 | 1.15 | 1.10 | 1.22 | 0.62 | 0.73 |
| TMZ-Sensitive | | | | | | | | | | | | |
| U251 | 1.00 | 1.48 | 1.59 | 1.56 | 1.00 | 1.32 | 1.22 | 1.24 | 1.10 | 1.11 | 0.81 | 1.16 |
| LN229 | 1.00 | 1.41 | 1.09 | 2.03 | — | — | — | — | 1.10 | 1.22 | 0.62 | 0.73 |

N = 2 for each cell treatment group.

TABLE 4

$IC_{50}$ values for human GBM cells treated with either TMZ alone (0, 0.1, 1, 10, 100 or 1000 µM) or TMZ combined with OKN (1 mM).

| Cell line | TMZ, µM | TMZ, µM + OKN-007 |
|---|---|---|
| G55 (low) | 567.4 | 63.4 |
| G55 (high) | 94.3 | 37.9 |
| U138 | 448.1 | 195.5 |
| U251 | 176.5 | 8.0 |
| LN229 | 107.5 | Less 1 (<1) |
|  | ~100 | Less 1 (<1) |

ELISA established protein levels (Table 6) indicated that HIF-1a was elevated in most cells treated with TMZ or combined treatment. OKN-007 decreased HIF-1a levels slightly in U138 cells, whereas in all other cells this protein was slightly elevated in this treatment group. MGMT was elevated in G55, T98 and U251 cells treated with TMZ or combined treatment. OKN-007 slightly decreased MGMT in G55 and LN18 cells. MPG was mainly only elevated in U251 cells treated with TMZ or OKN-007 combined with TMZ. OKN-007 decreased MPG levels in LN229 cells.

TABLE 6

ELISA protein level (ng/mg cell lysate) changes for HIF-1α, MGMT and MPG in TMZ-resistant and TMZ-sensitive human GBM cells treated with either TMZ, OKN or combined OKN + TMZ, or untreated (UT).

| Cells | HIF-1α | | | | MGMT | | | | MPG | | | |
|---|---|---|---|---|---|---|---|---|---|---|---|---|
|  | UT | TMZ | OKN | Comb | UT | TMZ | OKN | Comb | UT | TMZ | OKN | Comb |
| TMZ-Resistant | | | | | | | | | | | | |
| G55 | 0.14 | 1.08 | 0.19 | 1.13 | 0.37 | 1.19 | 0.31 | 1.11 | 1.15 | 1.50 | 1.41 | 1.77 |
| LN18 | 0 76 | 0.83 | 0.92 | 1.07 | 1.23 | 1.28 | 0.98 | 1.31 | 2.18 | 2.27 | 2.38 | 2.20 |
| U138 | 0.40 | 0.84 | 0.33 | 0.44 | 0.77 | 0.98 | 0.75 | 0.93 | 1.30 | 1.50 | 1.22 | 1.30 |
| T98 | 0.42 | 0.77 | 0.58 | 0.59 | 0.62 | 1.76 | 0.84 | 1.57 | 3.04 | 3.82 | 3.61 | 3.27 |
| TMZ-Sensitive | | | | | | | | | | | | |
| U251 | 0.30 | 1.41 | 0.61 | 0.91 | 0.92 | 1.48 | 0.91 | 1.44 | 2.70 | 4.99 | 2.77 | 4.09 |
| LN229 | 0.68 | 0.74 | 0.66 | 1.14 | 0.67 | 0.75 | 0.69 | 0.89 | 2.34 | 1.93 | 1.88 | 2.23 |

N = 2 for each cell treatment group.

Figure 17:
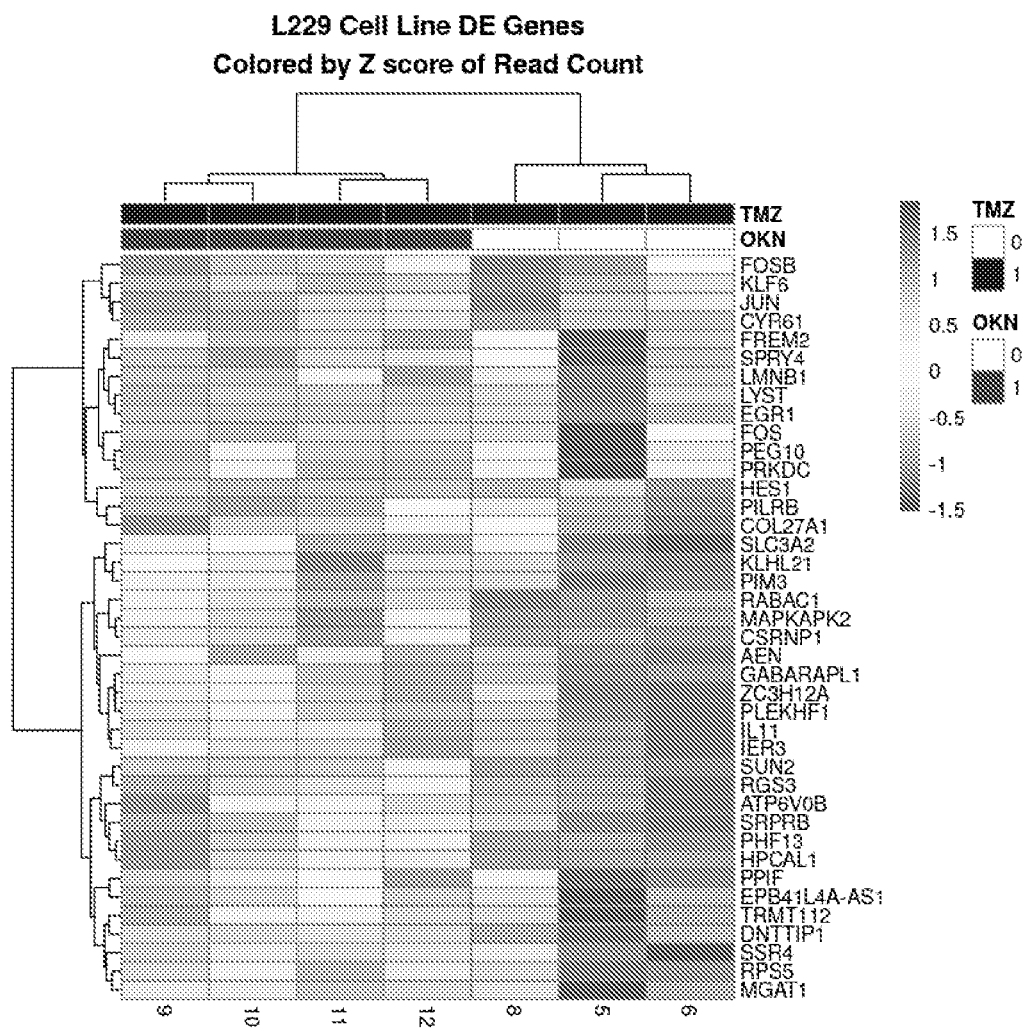
FIG. 17: Gene-fold changes when comparing TMZ+OKN to TMZ alone treatment groups in LN229 GBM cells.
Figure 18:
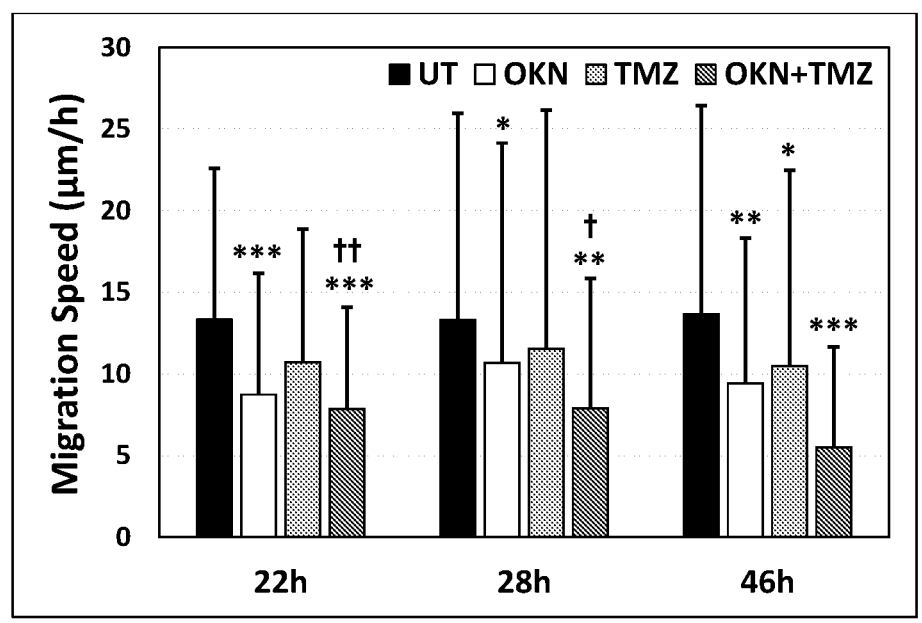
FIG. 18: Migration speeds of G55 GBM cells in PDMS (polydimethylsiloxane) micro-channels coated with laminin, either untreated (UT), or treated with either OKN-007 (OKN), TMZ or both OKN+TMZ, at 22, 28 and 46 h post-treatment. There was a significant difference between UT cells (*) and those treated with OKN or OKN+TMZ at 22 and 28 h, and with all treatment groups at 46h. There was a significant difference between TMZ and OKN+TMZ groups (†) at 22 and 28 h. *(†) $p<0.05$, (††) $p<0.01$, * $p<0.001$.
Figure 19:
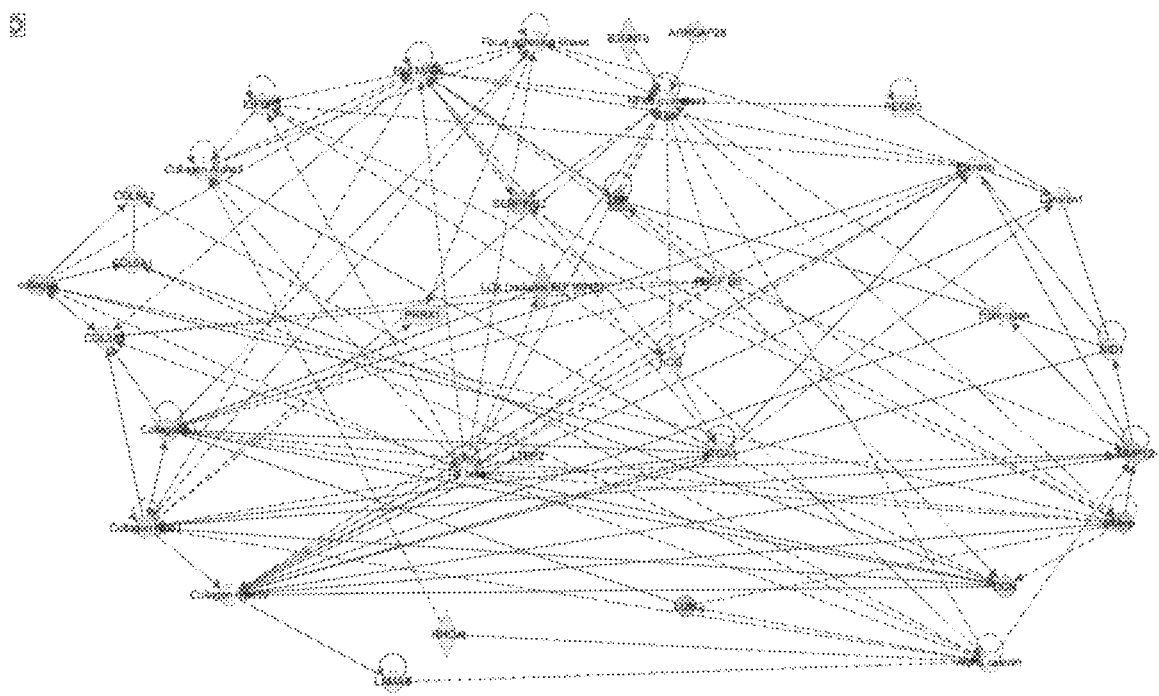
FIG. 19: Microarray analysis of mRNA samples from OKN-007-treated and untreated rat F98 glioma-bearing tumors, indicating down-regulated genes (green; >2-fold change) in the treated group (n=4) compared to the untreated group (n=4) in a network pathway schematic. Major down-regulated gene pathways affected include TGFβ1, PDGFBB, P38 MAPK, NFKB, some MMPs (particularly MMP12), DCN (decorin), SERPINB2, LUM, LBP (lipopolysaccharide binding protein), and several collagens.

RNA-seq data. FIG. 17 shows that the LN18 cells had 37 upregulated genes, and 3 genes down-regulated in the TMZ+OKN group compared to TMZ alone group. For sample 25 the genes seem to be all upregulated in this column. This seems to be set at a different threshold than the other combined OKN+TMZ LN18 samples. If the threshold was reduced, then the pattern would be similar to those in columns 26 or 28 (the other combined OKN-007+TMZ treated LN18 cells).

Figure 16:
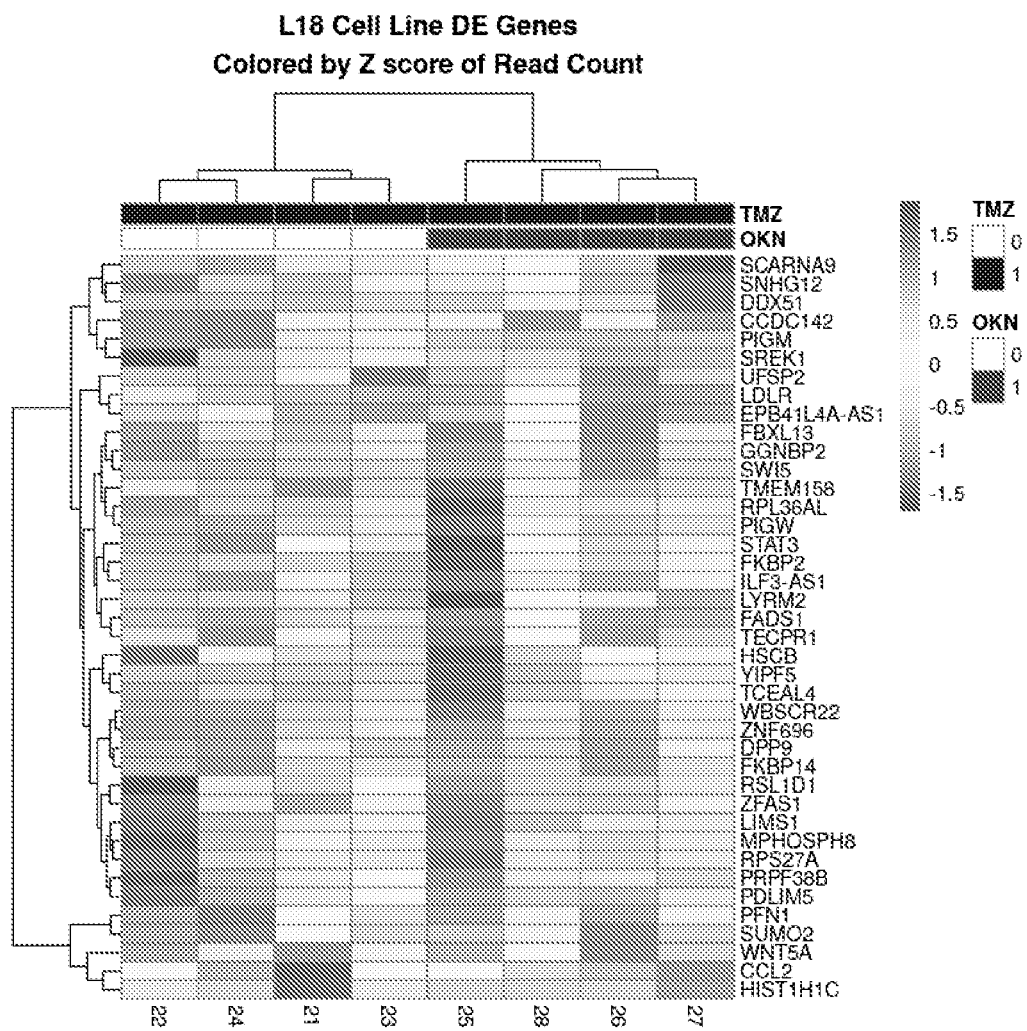
FIG. 16: Gene-fold changes when comparing TMZ+OKN to TMZ alone treatment groups in LN18 GBM cells.

FIG. 16 shows that the LN18 cells had 37 upregulated genes, and 3 genes down-regulated in the TMZ+OKN group compared to TMZ alone group. For sample 25 the genes seem to be all upregulated in this column. This seems to be set at a different threshold than the other combined OKN+TMZ LN18 samples. If the threshold was reduced, then the pattern would be similar to those in columns 26 or 28 (the other combined OKN-007+TMZ treated LN18 cells). FIG. 17 shows that the LN229 cells had 21 upregulated genes, and 19 genes down-regulated in the TMZ+OKN group compared to TMZ alone group.

In vitro cell migration study. G55 GBM cell migration studies indicated that the cell migration speed for OKN-treated cells was significantly decreased at 22 h and 46 h following treatment, compared to untreated (UT) cells. Cells treated with TMZ were found to be significantly decreased at 28 h and 46 h following treatment, compared to UT cells. It was also found that combined OKN+TMZ treatments significantly decreased cell migration at 22 h and 28 h following treatment, compared to TMZ alone.

Microarray data from rat F98 gliomas either UT or treated with OKN-007. Microarray analysis identified predominant downregulation of genes following OKN treatment. 384 genes had at least one exon significantly downregulated, while only 3 were upregulated (data not shown). Pathway analysis indicated that OKN-treated F98 tumors downregulated several genes associated with the extracellular matrix (ECM) (e.g., collagen and MMP genes), all with a connection to TGFβ1.

RT-PCR was able to confirm that several ECM genes were downregulated with OKN-treatment, compared to UT F98 tumors (Table 7).

TABLE 7

RT-PCR of RNA isolated from F98 untreated and OKN-007-treated tumors with 2-, 5- or 10-fold changes in gene expressions.

| | Up-regulated | | | | Down-regulated | | |
|---|---|---|---|---|---|---|---|
| Gene | >2-fold | >5-fold | >10-fold | Gene | >2-fold | >5-fold | >10-fold |
| CDH4 | 4.06 | | | ADAMTS1 | 3.57 | | |
| CNTN1 | | | 15.03 | CD44 | 3.03 | | |
| HAPLN1 | 3.1 | | | CDH3 | 3.70 | | |
| MMP16 | 4.72 | | | COL1A1 | 2.27 | | |
| NCAM2 | | | 11.63 | COL2A1 | 2.33 | | |
| SGCE | | 8.06 | | COL3A1 | 3.13 | | |
| SPOC1 | | | 11.08 | COL4A1 | 2.94 | | |
| SYT1 | | | 19.03 | COL4A2 | 2.63 | | |
| VTN | 3.03 | | | COL5A1 | 3.33 | | |
| | | | | COL6A1 | 2.94 | | |
| | | | | COL8A1 | 2.33 | | |
| | | | | CTGF | 2.63 | | |
| | | | | ECM1 | 2.86 | | |
| | | | | EMILIN1 | 2.27 | | |
| | | | | FN1 | 2.63 | | |
| | | | | ITGA2 | 3.7 | | |
| | | | | ITAD | 2.38 | | |
| | | | | ITGB3 | 2.13 | | |
| | | | | ITGB3 | 2.13 | | |
| | | | | ITGB4 | 3.70 | | |
| | | | | LAMC1 | 2.33 | | |
| | | | | MMP12 | | | 16.67 |

TABLE 7-continued

RT-PCR of RNA isolated from F98 untreated and OKN-007-treated tumors
with 2-, 5- or 10-fold changes in gene expressions.

| | Up-regulated | | | Down-regulated | | |
|------|---------|---------|----------|-------|---------|---------|----------|
| Gene | >2-fold | >5-fold | >10-fold | Gene | >2-fold | >5-fold | >10-fold |
| | | | | MMP13 | | | 50.00 |
| | | | | MMP14 | 2.86 | | |
| | | | | MMP1 A | 4.17 | | |
| | | | | MMP2 | 2.86 | | |
| | | | | MMP3 | 3.85 | | |
| | | | | MMP7 | 2.86 | | |
| | | | | MMP8 | 3.85 | | |
| | | | | MMP9 | | 7.14 | |
| | | | | POSTN | | | 33.33 |
| | | | | SELE | 2.86 | | |
| | | | | SELL | 2.13 | | |
| | | | | SELP | 2.13 | | |
| | | | | SPP1 | | 8.33 | |
| | | | | TGFBI | 2.22 | | |
| | | | | THBS2 | 3.7 | | |
| | | | | TIMP1 | 3.45 | | |
| | | | | RGDC | 3.45 | | |

Figure 20:
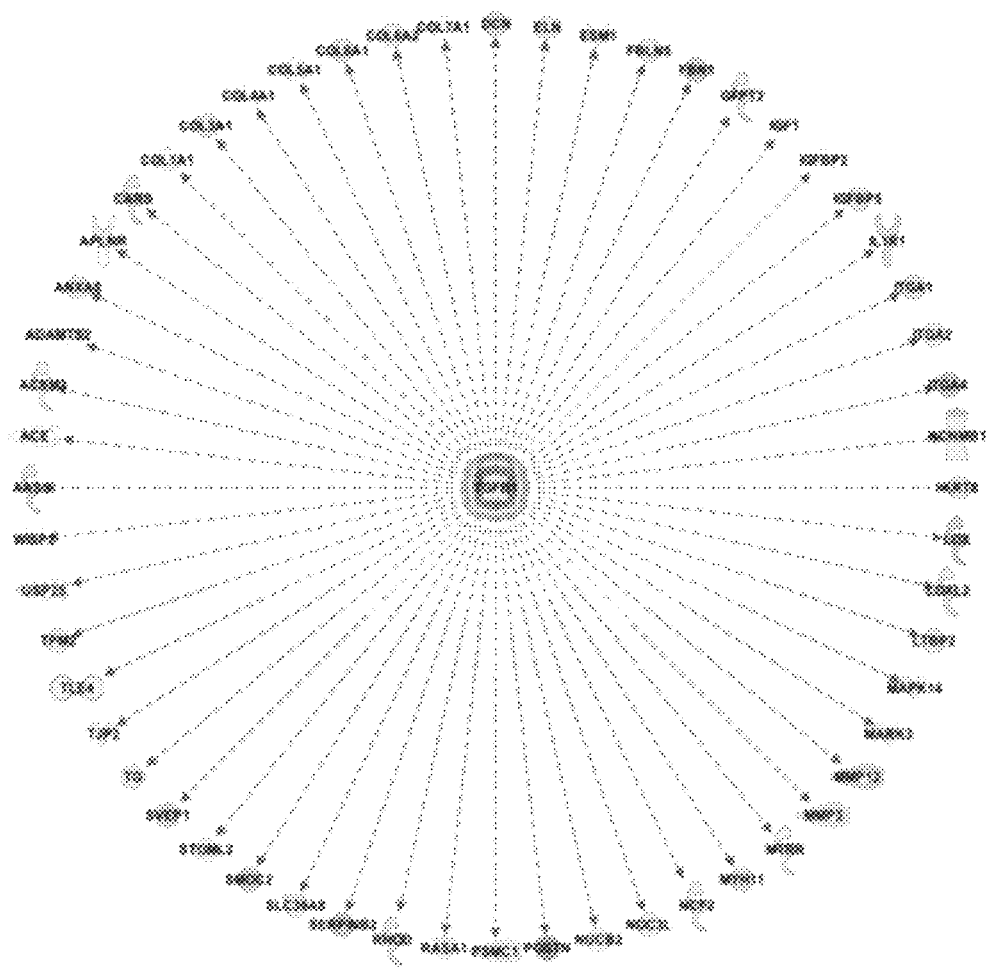
FIG. 20: TGFβ1 as a master regulator of 57 down-regulated genes by OKN-007 in rat F98 treated gliomas vs. untreated tumors. (Upstream Regulator Analysis, IPA). OKN-007 down-regulates 57 genes including collagens, MMP12 (tissue remodeling), SERPINB2 (serpin peptidase inhibitor), IGFBP5 (insulin-like growth factor binding protein).

Upstream regulator analysis identified TGFβ1 as the most significant inhibited upstream regulator, controlling 57 downregulated genes (FIG. 20). TGFβ1 was itself down-regulated nearly 2-fold.

Immunohistochemistry showed that TGFβ1 protein levels were substantially reduced in OKN-treated F98 gliomas, compared to UT tumors (FIGS. 21A-B). The decrease in TGFβ1 protein levels was also confirmed using ELISA, indicating a significantly decreased ($p<0.001$) level of TGFβ1 protein expression in OKN-treated F98 gliomas, compared to UT tumors (FIG. 21C).

Example 6

Discussion

The inventors were able to establish that OKN-007 when combined with TMZ can augment the effect of TMZ in TMZ-sensitive GBM cells, as well as render TMZ-resistant GBM cells more sensitive to TMZ and/or the effect of OKN-007 on tumor cell growth. They were able to establish that OKN-007, by itself, can down-regulate several genes associated with the extracellular matrix through TGF-β1, and also be effective against cell migration. They previously found that OKN-007 can effectively inhibit cell proliferation, decrease HIF-1a and VEGFR2, which are both associated with angiogenesis, and increase apoptosis. When OKN-007 is combined with TMZ, it can be effective against both TMZ-sensitive and TMZ-resistant GBM cells in vitro, and synergistically decrease tumor volumes, as well as increase animal survival and normal vascularization in vivo in a G55 orthotopic xenograft GBM model.

Other TMZ combined therapies that have been recently investigated include: silencing GLI1, which is associated with Hedgehog signaling, and specifically affected glioma-like stem cells (U87-MG, T98G) (Melamed et al., 2018); inhibiting Wnt/β-catenin signaling, which downregulates the expression of aldehyde dehydrogenase isoform 3A1 (ALDH3A1) (Suwala et al., 2018); using a miR-519a mimic, where miR-519a functions as a tumor suppressor by targeting the signal transducer and activator of transcription 3 (STAT3)-mediated autophagy, and promoting TMZ-induced autophagy (U87-MG/TMZ) (Li et al., 2018); inhibiting PI3K to sensitize GBM cells to TMZ (Haas et al., 2018); inhibiting the SOX9/CA9 (carbonic anhydrase 9)-mediated oncogenic pathway to enhance TMZ-sensitivity (Xu et al., 2018); and co-delivery of TMZ and siRNA targeting the BCL-2 gene using a folate-conjugated triblock copolymer (Fa-PEG-PEI-PCL, Fa-PEC) of poly(ε-caprolactone) (PCL), poly(ethylenimine) (PEI) and poly(ethylene glycol) (PEG) nanocarrier construct (Peng et al., 2018). All of the therapies combined with TMZ either are used to augment the effect of TMZ and/or effect TMZ-resistant GBM cells.

For the $IC_{50}$ component of the study, for all cells, OKN-007 had a substantial effect in reducing the TMZ IC50 concentration, so that the GBM cells all became TMZ-sensitive (or more TMZ-sensitive if they already were). There should be a cautionary note regarding assessing TMZ-resistance with the G55 cells. The inventors established that a low-passage G55 cell line is actually TMZ-resistant, whereas high-passage G55 (>30 passages) may become TMZ-sensitive. For the in vivo G55 xenograft data, the inventors used a low-passage G55 cell line (<10 passages), which were a similar passage to those used for the inventors' in vitro studies.

From the varying concentrations of OKN-007, it was concluded that a concentration of 1 mM OKN was just as effective in reducing cell viabilities, compared to the 2 mM concentration for some cell lines (e.g., LN229, U138, G55), whereas for other cell lines (e.g., U251, T98, LN18) 2 mM OKN was slightly more effective in reducing cell viabilities, compared to the 1 mM concentration.

Protein levels seem to indicate that TMZ elevates HIF-1a in all cells, elevates MGMT in most cells (except LN229), and elevates MPG in only T98 and U251 cells. OKN-007 for most cells seems to not affect HIF-1a protein (compared to in untreated cells), that OKN-007 by itself seems to not effect protein levels of MGMT (compared to untreated cells; except LN18), and that MPG is still elevated in T98 cells with OKN treatment alone. Of interest, HIF-1a was induced by TMZ in U251, U138, and T98 cells, and then decreased by OKN-007. Combined TMZ+OKN seems to keep HIF-1a elevated (except for U138 cells), that MGMT protein levels were not substantially changed with combined TMZ+OKN treatment, and that MPG is still elevated in U251 cells with combined TMZ+OKN treatment, whereas other cells are not substantially affected (from either TMZ, OKN or combined TMZ+OKN treatments). Specifically, in U251, T98, and G55 cells, the level of MGMT increased due to TMZ, but the treatment of OKN-007 did not inhibit the expression of MGMT.

At the gene level, for TMZ-treated cells, HIF-1a gene-fold changes increase in all cells (compared to untreated cells). Combined TMZ+OKN treatment results in some cells increasing HIF-1a gene-fold changes more so than TMZ alone (e.g., LN229, LN18, U138 and G55), but overall, there does not seem to be any substantial decreasing effect on HIF-1α with combined treatment. There is noted reduced HIF-1α gene expression due to combined treatment in T98, but it was not significant. OKN alone seems to only decrease HIF-1α gene-fold changes in the T98 GBM cells compared to untreated cells. HIF-1a gene-fold changes in OKN treatment for U138 and U251 seems to still be increased (compared to untreated cells). Unlike protein levels, there is no reduction in HIF-1α by OKN-007 at the gene level. There was a reduction effect of OKN-007 only in T98 cells. HIF-1a gene-fold changes may differ in a more hypoxic environment, such as in a tumor (in vivo), compared to the normoxic conditions in cells.

There were only modest increases in MGMT gene-fold changes for TMZ alone or combined TMZ+OKN in only 3 cell lines (U251, T98, LN18) that had detectable levels. OKN treatment alone slightly increased MGMT gene-fold changes in U251 cells, but conversely decreased MGMT gene-fold changes in LN18 and T98 cells (compared to untreated cells). Regarding OKN, these results may indicate that OKN alone may decrease MGMT gene expression, which may decrease resistant for GBM cells.

MPG gene-fold changes (unlike the protein levels) in TMZ treated cells were elevated more than 2-fold in 3 cell lines (G55, LN18 and U138). With combined therapy, 4 cell lines (G55, LN229, LN18 and U138) had elevated MPG gene-fold changes (compared to untreated cells). Of interest, OKN treatment alone had continued elevated MPG gene-fold changes for 2 cell lines (G55 and U138), and some decreases for 2 other cell lines (LN18, T98) (compared to untreated cells). There were no decreases in MGT by OKN-007 that were observed.

From the RNA-seq data for LN18 GBM cells, interesting upregulated genes are RNF149 (stress sensor gene that amplifies p53 response to arrest cell cycle), IDO-1 (involved in human gliomas), and SLC14a2 (endogenous transmembrane protein upstream-of-mTORC2 (UT2) negatively regulates activation of STAT3). Interesting down-regulated genes include SUMO2 (overexpression of SUMO in conditions such as brain ischemia and hypoxia, could increase cell survival whereas the knockdown of SUMO expression has proven to be toxic to cells; and associated with TGFβ1 in resistant glioma cells (Yoshino et al., 2010), HIST1H1C/H1.2 (knockdown of histone HIST1H1C inhibits high glucose induced inflammation and cell toxicity), and PFN1 (profiling-1 phosphorylation is associated with tumor aggressiveness in human glioma) (Liu et al., 2012).

For RNA-seq data for the LN229 cells, interesting down-regulated genes are EGR1 (associated with shorter disease-free survival in patients whose tumors are ER positive and HER2 positive; IGF1R signaling pathway is very relevant in drug resistance), XIST (increased level associated with shorter survival and poorer prognosis), and PRKDC (prognostic biomarker for chemoresistance in breast cancer patients). Interesting up-regulated genes include ZC3H12A (crucial negative regulator of inflammation), RN7SK (potential anti-proliferative and tumor-suppressive function), SUN-2, and KLHL21.

From further bioinformatics analysis, FOS has the most robust down-regulation, which can be observed as an OKN effect across all cell lines, and all treatment conditions TMZ, OKN, and TMZ+OKN, as well as when the data is separated into each treatment condition or cell line separately. FOS has also been observed to be sufficient for decreasing cell viability and sensitizing glioblastoma to DNA damage via radiation, so it is possible that this may be helping TMZ cause DNA damage as well (Liu et al., 2016).

MGMT had non-significant changes in many of the conditions; however, for LN229, the loge fold change was ~3 with a p-value of ~0.057.

Other MOA that could be associated with TMZ-resistance and that combined OKN+TMZ therapy may be affecting include TGF-β1 (Yoshino et al., 2010; Wang et al., 2017), and also possibly Akt (Fan et al., 2014), and macrophages (Zeng et al., 2017). In the inventors' microarray assessment of F98 rat gliomas treated with OKN, TGF-β1 played a major role in the MOA for OKN efficacy, by down-regulating 57 genes that are commonly linked to TGF-β1. Perhaps in combined OKN+TMZ therapy, OKN is affecting TGF-β1 and eliciting a response on TMZ-resistant cells.

From microarray analysis of OKN-007-treated vs. untreated rat F98 glioma RNA, it was established that downregulated genes mainly included members of integrin and collagen families, which are enriched in the extracellular matrix1 and cell adhesion. Cell viability of tumor tissues treated with OKN-007 was decreased, whereas cell death was increased via the downregulation of ANGPT2, DLL4, HPX, IGF1 and TGFB1 genes. "Angiogenesis" was also decreased in OKN-007-treated samples. Several immune response genes were notably downregulated, with LBP (lipopolysaccharide binding protein) being the most downregulated.

TGFB1, the last exon of which was downregulated, was the master regulator of 57 genes. It participates in nearly all processes mentioned above, and as such may be considered as the main upstream regulator downregulated by OKN-007.

In addition to integrins and collagens there's notable group of extracellular matrix glycoproteins, such as lumican (LUM), fibrillin1 and 5 (FBN1), laminin (LAMA2). All of them are downregulated, however, matrix metallopeptidase 3 (MMP3), an enzyme degrading all aforementioned proteins, ADAMTS9 and PRSS2, other peptidases, are also downregulated. CD248, expressed in vascular endothelial cells of malignant tumors but not in normal blood vessels, is downregulated. That suggests extracellular matrix maintenance and remodeling is active in untreated glioma samples, and is normalized by OKN-007 treatment.

TGFB1 and a member of TGF-beta proteins LTBP2 (latent transforming growth factor beta binding protein) regulating cell adhesion and migration among other functions, are also downregulated. Similarly, other cell adhesion-related molecules, such as POSTN (periostin) and LUM (lumican) are downregulated. F11r (F11 receptor), an immunoglobulin superfamily gene member, is an important regulator of cell adhesion, cell-cell interaction, and formation of tight junction, —is also downregulated. Collectively, it is suggestive that cell adhesion is downregulated.

LBP (lipopolysaccharide binding protein) is the strongest downregulated immune-related gene, and majority of its exons are downregulated. This gene is involved in the acute-phase immunologic response to gram-negative 8 bacterial infections. DMBT1 (deleted in malignant brain tumors 1) play a role in the interaction of tumor cells and the immune system. Cytokine receptor IL1R1, oncostatin M receptor (OSMR), which heterosimerizes with IL6 and IL31AR, interferon (alpha, beta and omega) receptor 1 (IFNAR1), and F11 receptors are all downregulated.

Overall, processes overrepresented by downregulated genes appear to be brought back to a normal state, in contrast with untreated glioma samples, where they are aberrantly regulated. For example, the single-exon CD248 gene is highly expressed in malignant tumors (and in the untreated glioma samples from this study). CD248 was downregulated in OKN-007 treated samples, suggesting a reversal of the tumor cells back to a normal state.

As gliomas are highly invasive tumors, the inventors also used microfluidic chambers to see if OKN-007 not only had a role in inhibiting cell proliferation, angiogenesis and increasing apoptosis (Towner et al., 2013), but also has a role in inhibiting glioma cell migration/invasion (Szopa et al., 2017). The inventors showed that OKN-007 significantly decreased migration velocity. Glioma cell invasion is dependent on the interaction between the glioma cells and extracellular matrix components such as fibronectin, collagen IV, tenascin-C and fibronectin that stimulate different downstream migration pathways (Demuth and Berens, 2004).

As TGF-β1 plays a major role in TMZ-resistance (Yoshino et al., 2010; Wang et al., 2017), and OKN-007 may actually be affecting TMZ-resistance by targeting TGF-β1. Additional supportive data in the LN18 RNA-seq data shows that SUMO2, which is associated with TGF-β1 TMZ-resistance, is also knocked down when OKN is combined with TMZ (compared to TMZ alone).

Based on the in vitro combined OKN-007+TMZ treatment studies, for future studies, the following biomarkers, HIF-1α, TGFβ1, c-FOS, PFN-1, SUMO2, all need to be further pursued as potential key molecular components that may be involved in the role that OKN-007 may play in synergistically affecting TMZ-resistance, when combined with TMZ.

It should be noted that in previous studies for U251 and U87 cell lines, that gene expression profiles generated from tissue culture were significantly different from those generated from a subcutaneous (s.c.) implanted tumor, which was significantly different from those grown intracerebrally (i.c.). The disparity between the i.c gene expression profiles and those generated from s.c. xenografts suggests that whereas an in vivo growth environment modulates gene expression, orthotopic growth conditions induce a different set of modifications (Camphausen et al., 2005). This may imply the importance of using an appropriate model to correctly represent the tumor microenvironment (TME).

In conclusion, OKN-007 is an interesting anti-glioma agent, which not only can be effective on its' own, by targeting the tumorigenic TGFβ1 pathway via downregulation of key genes associated with the extracellular matrix and cell invasion, but also can elicit an effect on TMZ-resistance GBM cells/tissues. The MOA associated with combined OKN-007+TMZ therapy does not seem to occur via either HIF-1α, MGMT or MPG. OKN-007 itself did decrease some of these genes and proteins for some of the GBM cells, but the majority of GBM cells were either not affected or had elevated levels, with both OKN-007 or combined treatment groups. RNA-seq analysis provided some insights to other possible MOAs regarding how OKN-007 may play a role on TMZ-resistance when combined with TMZ, and these will need to be further pursued. Combining OKN-007 with TMZ seems like a promising therapeutic strategy that may prevent TMZ-resistant GBM cells from proliferating, and possibly extending the effect of TMZ.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Publication 2007/0032453
U.S. Pat. No. 5,569,902
U.S. Pat. No. 5,488,145
Bigner et al., In: *Pathology of Tumors of the Nervous System*, Russell and Rubinstein (Eds.), 6th Edition, London:Edward Arnold, 757, 1998.
Burger et al., In: *Surgical Pathology of the Nervous System and Its Coverings*, 3$^{rd}$ ed., New York, Churchill Livingstone, Inc, 737, 1991.
Burger et al., *Cancer,* 56:1106-1111, 1985.
Burger et al., *Cancer,* 59:1345-1352, 1987.
Cao et al., *Brain Res.,* 644:267-272, 1994.
Cao et al., *J Clin. Oncol.* 23:4127-36, 2005.
Carney et al., *Proc. Natl. Acad. Sci. USA,* 88:3633-3636, 1991.
Clough-Helfman et al., *Free Radic. Res. Commun.,* 15:177-186, 1991.
Coutinho de Souza et al., *Free Radic. Biol. Med.,* 87:157-168, 2015.
Daumas-Duport et al., *J. Neurooncol.,* 34:61-78, 1997.
Davis et al., *J. Neurooncol.,* 24:9-12, 1995.
Dehghani et al., *Acta Neuropathol.,* 95:493-504, 1998.
Doblas et al., *Free Radic. Biol. Med.* 44:63-72, 2008.
Floyd et al., *FASEB J.,* 4:2587-2597, 1990.
Floyd et al., In: *Neuroprotective Approaches to the Treatment of Parkinson's Disease and other Neurodegenerative Disorders*, Chapman et al. (Eds.), Academic Press Limited, London, 69-90, 1996.
Floyd, *Adv. Pharmacol.,* 38:361-378, 1997.
Folbergrova et al., *Proc. Natl. Acad. Sci. USA,* 92:5057-5061, 1995.
Fosmark et al., *PLoS ONE* 12(6): 1-17, 2017.
Heegard et al., *Cancer,* 76:1809-1813, 1995.
Hensley et al., In: *Neuroprotective Agents and Cerebral Ischaemia*, Green and Cross (Eds.), Academic press Ltd., London, 299-317, 1996.
Hoshino et al., *Int. J. Cancer,* 53:550-555, 1993.
Kleihues and Cavenee, In: *Pathology and Genetics of Tumors of the Nervous System*, IARC Press, Lyon, 227-228, 2000.
Kleihues and Ohgaki, *Brain Pathol,* 7:1131-1136, 1997.
Kleihues and Ohgaki, *Neuro-Oncology,* 1:44-51, 1999.

Kleihues et al., In: *Histological Typing of Tumours of the Central Nervous System*, 2$^{nd}$ Ed., Berlin: Springer-Verlag, 112, 1993.
Kros et al., *Cancer,* 78:1107-1113, 1996.
Lamborn et al., *Cancer,* 85:925-935, 1999.
Muller et al., *Acta Neurochir* (Wien), 37:75-91, 1977.
Pahlmark et al., *Acta Physiol. Scand.,* 157:41-51, 1996.
Pogrebniak et al., *Surgery,* 112:130-139, 1992.
Poyer et al., *Biochim. Biophys. Acta,* 539:402-409, 1978.
Schneider et al., *Acta Neuropathol* 107:272-6, 2004.
Shaw et al., *Neurosurgery,* 34:577-582, 1994.
Wacker et al., *J. Neuro-Oncology,* 19:113-122, 1994.
Wang and Shuaib, *Drugs Aging* 24:537-46, 2007.
Ostrom Q T, Gittleman H, Liao P et al., CBTRUS Statistical Report: Primary brain and other central nervous system tumors diagnosed in the United States in 2010-2014. Neuro Oncol 2017; 19: vl-v88.
Lai S W, Huang B R, Liu Y S, Lin H Y, Chen C C, Tsai C F, Lu D Y, Lin C. Int J Mol Sci 2018; 19(1).
Shi Jet al., Oncotarget 2017; 8 (50): 87554-567.
Fisher T et al., Cancer J 2007; 13: 335-344.
Furnari FB, Fenton T, Bachoo RM et al., Genes Dev 2007; 21: 2683-2710.
Liu Z-G et al., cOncotarget 2016; 7 (40): 65946.
Happold C, Stojcheva N, Silginer M, Weiss T, Roth P, Reifenberger G, Weller M. J Neurochem 2018; 144 (6): 780-790.
Wang Z, Xu X, Liu N, Cheng Y, Jin W, Zhang P, Wang X, Yang H, Liu H, Tu Y. Oncotarget 2017; 9 (1): 192-204.
Zhao Y H et al., Front Neurol 2018; 9: 127.
Tang JB et al., Neuro Oncol 2011 13 (5): 471-86.
Tang J H et al., Exp Cell Res 2016; 343 (2): 148-158.
Melamed J R, Morgan J T, Ioele S A, Gleghorn J P, Sims-Mourtada J, Day E S. Oncotarget 2018; 9(43): 27000-27015.
Grek C L, Sheng Z, Naus C C, Sin W C, Gourdie R G, Ghatnekar G G. Curr Opin Pharmacol 2018; 41: 79-88.
Haas B, Klinger V, Keksel C, Bonigut V, Kiefer D, Caspers J, Walther J, Wos-Maganga M, Weickhardt S, Rohn G, Timmer M, Frotschl R, Eckstein N. Cancer Cell Int 2018; 18: 69.
Xu X, Wang Z, Liu N, Cheng Y, Jin W, Zhang P, Wang X, Yang H, Liu H, Zhang Y, Tu Y. Int J Oncol 2018; 53(1): 189-202.
Dai S, Yan Y, Xu Z, Zeng S, Qian L, Hou L, Li X, Sun L, Gong Z. Front Pharmacol 2018; 8: 960.
Roos W P, Frohnapfel L, Quiros S, Ringel F, Kaina B. Cancer Lett 2018; 424: 119-126.
Shang C, Tang W, Pan C, Hu X, Hong Y. Cancer Chemother Pharmacol 2018; 81(4): 671-678.
Sun Q, Pei C, Li Q, Dong T, Xing W, Zhou P, Gong Y, Zhen Z, Gao Y, Xiao Y, Su J, Ren H.
Biochem Biophys Res Commun 2018; 496(4): 1040-1046.
Yi G Z, Xiang W, Feng W Y, Chen Z Y, Li Y M, Deng S Z, Guo M L, Zhao L, Sun X G, He M Y, Qi S T, Liu Y W. Biomed Res Int 2018; 2018: 5238760.
Jia L, Tian Y, Chen Y, Zhang G. Onco Targets Ther 2018; 11: 313-321.
Towner R A, Gillespie D L, Schwager A, Saunders D G, Smith N, Njoku C E, Krysiak R S III, Larabee C, Iqbal H, Floyd R A, Bourne D W A, Abdullah O, Hsu E W, Jensen R L. Neuro Oncology 15: 330-40 (2013).
Coutinho de Souza P, Balasubramanian K, Njoku C, Smith N, Gillespie DL, Schwager A, Abdullah O, Ritchey JW, Fung K-M, Saunders D, Jensen R L, Towner R A J Magn Reson Imaging, 2015; 42: 1582-91.
Coutinho de Souza P, Smith N, Pody R, He T, Njoku C, Silasi-Mansat R, Lupu F, Meek B, Chen H, Dong Y, Saunders D, Orock A, Hodges E, Colijn S, Mamedova N, Towner R A. Am J Nuclear Med Mol Imaging 2015; 5(4): 363-78.
Coutinho de Souza P, Smith N, Atolagbe O, Ziegler J, Nijoku C, Lerner M, Ehrenshaft M, Mason RP, Meek B, Plafker S M, Saunders D, Mamedova N, Towner R A. Free Radical Biol Med 2015; 87: 157-168.
Ziegler J, Pody R, Coutinho de Souza P, Evans B, Saunders D, Smith N, Mallory S, Njoku C, Dong Y, Chen H, Dong J, Lerner M, Mian O, Tummala S, Battiste J, Fung K-M, Wren J D, Towner R A. Neuro-Oncology 2017; 19(2): 175-185.
Griffins J, Tesiram Y, Reid G E, Saunders D, Floyd R A, Towner R A. J Lipid Res 2009; 50: 611-622.
Wright G W, Simon R. Bioinformatics 2003; 19: 2448-55.
Bushnell B.//sourceforge. net/projects/bbmap. 2014.
Andrews S. FastQC: a quality control tool for high throughput sequence data. 2010.
Ewels P, Magnusson M, Lundin Käller M. Bioinformatics 2016; 32(19): 3047-3048.
Trapnell C, Pachter L, Salzberg SL. Bioinformatics 2009; 25(9): 1105-1111.
Love M I, Huber W, Anders S. Genome Biology 2014; 15: 550. doi: 10.1186/s13059-014-0550-8.
Benjamini Y, Hochberg Y. J Royal Stat Soc Ser B 1995; 57(1): 289-300.
Robinson M D, McCarthy D J, Smyth G K. Bioinformatics 2010; 26(1): 139-140.
Suwala A K, Koch K, Rios D H, Aretz P, Uhlmann C, Ogorek I, Felsberg J, Reifenberger G, Kohrer K, Deenen R, Steiger H J, Kahlert U D, Maciaczyk J. Oncotarget 2018; 9(32): 22703-22716.
Li H, Chen L, Li J J, Zhou Q, Huang A, Liu W W, Wang K, Gao L, Qi S T, Lu Y T. J Hematol Oncol 2018; 11(1):70.
Peng Y, Huang J, Xiao H, Wu T, Shuai X. Int J Nanomedicine 2018; 13: 3467-3480.
Yoshino A et al., Int J Oncol 2010; 36(6):1367-77.
Liu C et al., J Biomed Biotechnol 2012; 2012:760679.
Wang Z et al., Anticancer Drugs 2017; 29: 136-144.
Fan Y et al., Nat Cell Biol 2014; 16 (5): 445-56.
Zeng H et al., Cell Death Dis 2017; 8 (6): e2885.
Szopa W, Burley T A, Kramer-Marek G, Kaspera W. Biomed Res Int 2017; 2017: 8013575.
Demuth T, Berens M E. J Neuro-Oncology 2004; 70 (2): 217-228.
Camphausen K et al., PNAS 2005, 102(23) 8287-8292.

The invention claimed is:

1. A method of treating a temozolomide-resistant glioma in a subject comprising administering to said subject a dose of 2,4-disulfonyl phenyl tert-butyl nitronc (2,4-ds-PBN) and temozolomide effective to inhibit the vascularization, growth or spread of said glioma.

2. The method of claim 1, wherein administration is through a route requiring subsequent passage of 2,4-ds-PBN across the blood brain barrier.

3. The method of claim 1, wherein the subject has a recurrent or metastatic glioma.

4. The method of claim 1, wherein the subject has previously failed one or more anti-glioma therapies.

5. The method of claim 1, wherein the effective dose of 2,4-ds-PBN is from about 5 to about 150 mg/kg body weight per day.

6. The method of claim 1, further comprising a secondary anti-glioma therapy.

7. The method of claim 1, wherein said glioma is an astrocytoma, an oligodendroglioma, or a glioblastoma multiforme, or a TGF-β1-, MGMT- and/or APGN-expressing form of any of the foregoing.

8. The method of claim 1, further comprising assessing therapeutic efficacy by measuring the expression of liposaccharide binding protein prior to and after a treatment with 2,4-ds-PBN.

9. The method of claim 2, wherein the route is enteral, intravenous, or intra-arterial.

10. The method of claim 2, wherein enteral administration is through dietary supplementation of a food component.

11. The method of claim 2, wherein the enteral administration is in the form of a pill or a liquid.

12. The method of claim 6, wherein the secondary anti-glioma therapy is radiation, surgery, or chemotherapy.

13. The method of claim 1, wherein an effective dose of temozolomide is lower than the standard monotherapy dose of temozolomide.

14. The method of claim 10, wherein the effective dose of 2,4-ds-PBN is from about 0.005 w/w % to about 0.1 w/w % of the diet being administered.

\* \* \* \* \*